United States Patent
Hetherington et al.

(10) Patent No.: US 7,550,261 B2
(45) Date of Patent: Jun. 23, 2009

(54) METHOD OF SCREENING FOR DRUG HYPERSENSITIVITY REACTION

(75) Inventors: Seth Hetherington, Alpharetta, GA (US); Arlene R Hughes, Durham, NC (US); Eric H Lai, Durham, NC (US); Michael Mosteller, Jr., Durham, NC (US); Denise D Shortino, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 671 days.

(21) Appl. No.: 10/214,023

(22) Filed: Aug. 7, 2002

(65) Prior Publication Data

US 2003/0096274 A1  May 22, 2003
US 2007/0148641 A9  Jun. 28, 2007

Related U.S. Application Data

(60) Provisional application No. 60/336,850, filed on Oct. 30, 2001, provisional application No. 60/314,026, filed on Aug. 21, 2001.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.1; 435/91.2; 536/24.3

(58) Field of Classification Search ....................... None
See application file for complete search history.

(56) References Cited

U.S. PATENT DOCUMENTS

2006/0046267 A1* 3/2006 Mallal ....................... 435/7.1

FOREIGN PATENT DOCUMENTS

EP  434 450 A2  6/1991

OTHER PUBLICATIONS

Mallal et al; The Lancet, vol 359, pp. 727-732; Mar. 2, 2002.*
Hetherington et al; Oral Abstract from 9th Conference on Retroviriruses, Feb. 24th, 2002.*
Hetherington et al; Lancet, vol 359, pp. 1121-1122, Mar. 30, 2002.*
Hughes et al; Pharmacogenomics, vol. 5, 2004, pp. 203-211.*
Hughes et al; Pharmacogenetics, 2004, 14:335.*
Rauch et al; Clin. Infect. Dis. 2006, 43:99.*
Martin et al; Pharmacogenomics; 7 :17, 2006.*
Martin et al ; PNAS, 101 :4180, 2004.*
D. Hughes et al: Pharmacogenetics, 2004, 14:335.*
Migueles et al: PNAS, Mar. 2000, vol 97, pp. 2709-2714.*
European Search for EP02756990.4 dated Jan. 4, 2005.
Vyakarnam et al., "Abacavir induced hypersensitivity in HIV infected individuals is associated with an increased frequency of Th0 cells" AIDS (Hagerstown) 14(4):S65 (Oct. 2000).
Hetherington et al., "Hypersensitivity reactions during therapy with abacavir: analysis of 636 cases for clinical presentation and risk factors" 7th Conference on Retroviruses and Opportunistic Infections, San Francisco, CA Jan. 30-Feb. 4, 2000.
Henry, Review of Oral Abstract Session 24 of the 9th Conference on Retroviruses and Opportunistic Infections, www.thebody.com/confs/rtro2002/henry2.html (retrieved from internet Oct. 5, 2005).
Hetherington et al., Genetic variation in HLA-B region and Hypersensitivity reactions to abacavir, The Lancet 359: 1121-1122 (Mar. 2002).
Hetherington et al., HLA-B57 and TNF-alpha Variants Associated with Hypersensitivity Reactions to Abacavir among HIV-1-Positive Subjects, 9th Conference on Retroviruses and Opportunistic Infections, (Feb. 2002) (Abstract).
Mallal et al., Association between presence of HLA-B*5701, HLA-DR7, and HLA-DQ3 and hypersensitivity to HIV-1 reverse-transcriptase inhibitor abacavir, The Lancet 359:727-732 (Mar. 2002).
Mallal et al., The Presence of HLA-B*5701, -DRMI*0701, and -DQ3 is Highly Predictive of Hypersensitivty to the HIV Reverse Transcriptase Inhibitor Abacavir, 9th Conference on Retroviruses and Opportunistic Infections, (Feb. 2002) (ABSTRACT).
Pirmohamed et al., TNFα promoter region gene polymorphisms in carbamazepine-hypersensitive patients, Neurology 56:890-896 (2001).
Pirmohamed et al., Genetic sysceptibility to adverse drug reactions, TRENDS in Pharmacological Sciences 22(6):298-305 (Jun. 2001).
Roses, Genome-Based Pharmacogenetics and the pharmaceutical Industry, Nature Reviews 1:541-549 (Jul. 2002).
Training Materials for Examining Patent Applications with Respect to 35 U.S.C. 112, First Paragraph-Enablement of Chemical/Biotechnical Applications (pp. 1-65), Copy printed from USPTO website (wwww.uspto.gov) on Sep. 27, 2007.
Taylor, Genetic testing for inherited breast and ovarian cancer syndromes: important concepts for the primary care physician, Postgrad Med J 77:11-15 (2001).
Phillips et al., Potential Role of Pharmacogenomics in Reducing Adverse Drug Reactions - A Systematic Review, *JAMA* 286(18):2270-2279 (Nov. 14, 2001).

* cited by examiner

*Primary Examiner*—Jehanne S Sitton
(74) *Attorney, Agent, or Firm*—Virginia G. Campen

(57) ABSTRACT

Methods of assessing the risk of clinical signs of hypersensitivity reaction to nucleoside antiviral compounds, including abacavir, are described. The methods include genotyping subjects for polymorphisms in the TNFα gene, the class 1 HLA genes, or a combination of both the TNFα and HLA genes.

18 Claims, No Drawings

SEQUENCE LISTING

<160> NUMBER OF SEQ ID NOS: 13

<210> SEQ ID NO 1
<211> LENGTH: 1183
<212> TYPE: DNA
<213> ORGANISM: Homo Sapiens

<400> SEQUENCE: 1

```
ggggaagcaa aggagaagct gagaagatga aggaaaagtc agggtctgga ggggcggggg    60
tcagggagct cctgggagat atggccacat gtagcggctc tgaggaatgg gttacaggag   120
acctctgggg agatgtgacc acagcaatgg gtaggagaat gtccagggct atggaagtcg   180
agtatgggga ccccccctta acgaagacag ggccatgtag agggccccag ggagtgaaag   240
agcctccagg acctccaggt atggaataca ggggacgttt aagaagatat ggccacacac   300
tggggccctg agaagtgaga gcttcatgaa aaaaatcagg gaccccagag ttccttggaa   360
gccaagactg aaaccagcat tatgagtctc cgggtcagaa tgaaagaaga gggcctgccc   420
cagtgggtc tgtgaattcc cggggtgat ttcactcccc ggggctgtcc caggcttgtc    480
cctgctaccc ccacccagcc tttcctgagg cctcaagcct gccaccaagc ccccagctcc   540
ttctccccgc agggacccaa acacaggcct caggactcaa cacagctttt ccctccaacc   600
ccgttttctc tccctcaagg actcagcttt ctgaagcccc tcccagttct agttctatct   660
ttttcctgca tcctgtctgg aagttagaag gaaacagacc acagacctgg tccccaaaag   720
aaatgagc aatagggtttt gagggggcatg gggacgggt tcagcctcca gggtcctaca   780
cacaaatcag tcagtggccc agaagacccc cctcggaatc ggagcaggga ggatggggag   840
tgtgaggggt atccttgatg cttgtgtgtc cccaactttc caaatcccg ccccgcgat    900
ggagaagaaa ccgagacaga aggtgcaggg cccactaccg cttcctccag atgagctcat   960
gggtttctcc accaaggaag ttttccgctg gttgaatgat tctttcccg ccctcctctc   1020
gccccaggga catataaagg cagttgttgg cacacccagc cagcagacgc tccctcagca   1080
aggacagcag aggaccagct aagaggggaga gaagcaactg cagacccccc ctgaaaacaa   1140
ccctcagacg ccacatcccc tgacaagctg ccaggcaggt tct                    1183

<210> SEQ ID NO 2
<211> LENGTH: 817
<212> TYPE: DNA
<213> ORGANISM: Homo Sapiens

<400> SEQUENCE: 2
agccccacag tcttcgttat aacctcacgg tgctgtccgg ggatggatct gtgcagtcag    60
ggtttctcgc tgagggacat ctggatggtc agcccttcct gcgctgtgac aggcagaaat   120
gcagggcaaa gccccaggga cagtgggcag aagatgtcct gggaaataag acatgggaca   180
gagagaccag ggacttgaca gggaacggaa aggacctcag gatgaccctg gctcatatca   240
aggaccagaa agaaggtgag agtcggcagg ggcaagagtg actggagagg ccttttccag   300
aaaagttagg ggcagagagc agggacctgt atctacccac tggatctggc tcaggctggg   360
ggtgaggaat gggggtcagt ggaactcagc agggaggtga gccggcactc agcccacaca   420
gggaggcatg gaggagggcc agggaggcgt acccccctggg ctgagttcct cacttgggtg   480
gaaaggtgat gggttcggga atggagaagt cactgctggg tggggcagg cttgcattcc    540
ctccaggaga ttagggtctg tgagatccat gaagacaaca gcaccaggag ctcccagcat   600
ttctactacg atggggagct cttcctctcc caaaacctgg agactgagga atggacaatg   660
ccccagtcct ccagagctca gaccttggcc atgaacgctg ggaatttctt gaaggaagat   720
gccatgaaga ccaagacaca ctatcacgct atgcatgcag actgcctgca ggaactacgg   780
cgatatctaa aatccggcgt agtcctgagg agaacag                            817

<210> SEQ ID NO 3
<211> LENGTH: 51
<212> TYPE: DNA
<213> ORGANISM: Homo Sapien

<400> SEQUENCE: 3
cactgggttt gttgcagtaa gccacytcga atgttgctgt agaattaaag t             51

<210> SEQ ID NO 4
<211> LENGTH: 12930
<212> TYPE: DNA
<213> ORGANISM: Homo Sapien

<400> SEQUENCE: 4
gggccatggg gctgggccgg gtcctgctgt ttctggccgt cgccttccct tttgcacccc    60
cggcagccgc cgctggtgag tgggggttcct gcggtcccc ggcggagcgg gagcggcggg   120
gcgttttccgg gggtccgggt gggttgccgc gagcgctgct cggtcagggc ggggctcagg   180
tgtgctgtct ggagtgcagg gagctggacg ccgcctgttc ccgccacacc tcagccctgc   240
tttcccatct cccgtctctt tttttttttt tttttttttt ctttctgaga cggagtctct   300
gtcgcctagg ctgtagtgca gtggcgcgat attggctcac tgcaagctcc gcctcccggg   360
ttcacgccat tctcctgcct cagcctccct agtagctggg actacaggcg cccgccacca   420
cgcccggcta attttttgtg tttttagtag atatgggtt tcaccgtgtt agtcaggatg   480
gtctcgatct cctgacctcg tgatccgccc gcctcggcct ccaaagtgc tgggattaca   540
ggcgtgagcc accgcgcccg acctcccgtc tcctttcagt cctcctgggg atcgcgcatc   600
acccgcattt tctggtctcc tcctgcactt gctctcctcg cctcctcctc gtctcctctc   660
acttttcgga caaaccagtc ttctgaggc cctgggctgct cctgtgaatg   720
gcattggaag gccgttccag cgcggccgct gaggcagcca cttccccgg tgctgggggc   780
ggatctcagg tccctgaagt cctgtcctct cccggagccg atgtgttctc agctcctggg   840
ccgcagctcc tggagttggg gccctccttt cttgggaccc ggaggtggtg cttcttgcta   900
ctgtgaggac tgtgggggt cctgactctc aagctgaggg gttggagtct gcaggctccg   960
```

```
ggcagaggat tcttcctgcg acttctgtca tccccagctc attctccct  cgcctccggc 1020
tccggggtc  ctctcctctc tcgcatccca ccctactaa  tgaccaatga tctaaggaca 1080
ccagattccc tctcacctcc tccctgccca tcttacgcg  ccctgggtcc ttttgctctc 1140
ccagctccct gctaccctt  cctgtgtgct gttctctgat ccatttctag agtgtcctct 1200
gccttcatcc cccgccccg  ccactgaagg tccctcctgc ctcctttatg ggccttttcct 1260
gcaagcagcc ttcactccgt gctgccccta tgcctcccca ttcccaaatg tccctgactc 1320
taacttctg  gtgctgcctt ttgtccgggg gggtcttccc tccatcccac tcccctccag 1380
accctaagg  agagccctga tgctaatggc agttgggcct taggcagggc gcagggcagc 1440
gcagatgccc cctcccctcc agtgcaggtg cctgctctgg gccctgcctc attgtggccc 1500
cttccccact ccttcatcct cagcctcacc ctcttgagga ccccaccctc cagcccacag 1560
gtgctggacc atccctcct  ggtccctccg ccctctcca  ccttgggacc ttgtgctgct 1620
cctatctctt gcccagctgc ctgggccct  cagcaagttc tcatctttca gtgggaaagt 1680
gggagtgctg gagcatatga cagtgctgag aatctttccc aagcccacc  ctcccccaga 1740
gcaccctccc ctcctgtcct cacctaccc  caagttctcc cacagtcact cctgccccat 1800
gctcatgccg ccctccagtt cttgctctgc ccatctcccc tcccaaccc  agacctaaaa 1860
caggctgttg ggccagctgt tccttgacct tccttctttt cttttggttc cttgaccca  1920
gtgggctctc actcccaca  ccgcatatct aaaatctgtt ttgcctgctc ttggggtgcc 1980
actgctcccc ctccagcatt actcctttg  gcaggtcctt cctcaggctg agaatctccc 2040
cctctacctt ggtttttctct ctctggccag cacccccact ccttgctttg ttttaattt  2100
ttaactttg  tttgggtacg tagtagatat gtatgtatat atttatgggg tacatggtag 2160
attttgacac aggcctacaa tatgtcataa tcacatcagg gtaaatggtt tatctatcac 2220
aacaagcatt tatccttct  ttgtgctaca aacaatccca ttatgctctt tcagttattt 2280
ttaaatgtac aataaattat tgttggctgt actcaccctg ctgtgctatc tactagatct 2340
tattcattct aactatattt ttgtacccat taaccatccg cactccccca ctcccccacta 2400
cccttctcag cctctggtaa tcgtcattcc attgtctctc cccatgaggt ccattgtttt 2460
aattttggc  tgccacaaat aagtgagaac atgcgaagtt tgtctctctg ggcctgggc  2520
ttatttcact tcacatgatg acctccagtt ctttgcaaat gacatggtgg ctgaatagta 2580
ctccacatac acgtgtgcac cacatttctct ttctccattc gtctgttgat ggacacttag 2640
gtcgcttgca gatcttggct attttgaata gtgctgcaat aaacatggaa aagtagatag 2700
ctctttaata taccgatttc ctttcttttg ggtatatgcc taacagtggg agtgctggag 2760
catatgacag ctctattata tttttagttt ttggaagaac ctccacatta tttcccacag 2820
tggttatact agtttacgtt cccaccaaca gtgtacaagg gttctctttt gctacatcct 2880
cgccaggatt ccttattgcc tgtcttctgg ataaaagcca gtttatctgg ggtgggatga 2940
tatctcgtag gagttttgat ttgccttcat ctgatgacga atgatgttga gcacctttg  3000
atatacctgt ttgccatttg tatgtcttct tttgagaaat gactattcag atcttttgct 3060
cattttaag  ttggattatt agatatttt  cctatagagt tgtttgagat cctttatatgt 3120
tttggttact aatcctttgt cagatgaata gtttgaaaat attttctccc attcttggat 3180
ggtctcttca ctttgtttat tgtttcctttt gctgtgcaga agcttttttaa cttgatatga 3240
tccatttat  gcattttttac tttggttgcc tgtgcttgtg gggtattact taaaaaatct 3300
ttgccagtcc aatatcttag agagtttccc caatgttttc ttttatagtt ttcatagttt 3360
gaggtcatag atttacatct ttaatccttt ttgattggat ttttatatgt ggtgagagat 3420
agggtccagt ttcattcttc tgcataagga tatctagttt cccccagcacc atttattgaa 3480
gagactctcc ttgccctgt  atgtgttctt ggtaactttg ttagaaataa cttcactgta 3540
gatatatgga tttgtttctg ggttctctat tctgtttcat tggtccgtgt gtctgttttt 3600
atgccactac cgtgctgttt tgattactct agctctgtag tataatttga agtcagataa 3660
tgtgattcct ctagttttgt tcttttttgtt caggggtagct ttatctattc tgggtttttt 3720
gtgattccat atacatttta ggattgtttt tctatttctg tgaagaatgt cattggtgtt 3780
ttgatagcaa ttgcattgaa tttgtagatt gctttgggta ggatggatat tttaacaaaa 3840
ttgattcttc cggctgggca cggtggctca ctcctgtaat cccagcactt gggaggccga 3900
agtcaggtgg atcacttgag atcaggagtt caagaccagc ctgatcaaca tggagaaacc 3960
ccgcctctac taaaaataca aaattagcca ggcgtggtgg catatgcctg taatcccagc 4020
tactcaggaa agctgaggca ggagaatcgc ttgaacccag gaggcagagg ttgtggtgag 4080
ctgagattgc accattgcac tccagcctgg gcaacaggag caaaactcca tctcagaaaa 4140
taaaaataaa cattgattct tccagtccat gaacatggaa tgccttttcc atttttgttg 4200
tcctcttcaa tgttttgcat cagtgcttta tagttttat  tggagagatc tttcacttct 4260
tcagttaagt ctattcctag gtatttattt ttatttgtag ctaatgaaaa tgggattcgt 4320
ttcttgattt cttttcaga  ttatttgctg ttagcacata gaaatgctat tgatttttgc 4380
atgttgattt tgtatcctgc aactttactg aatttgtttct tcagttctaa tagttttttg 4440
gtggagtctt taggttttcc aaatatcaga ccacatgatg tgcaaacaag gataatttga 4500
cttcttcttt tccaattttg atgcccttta tttccttctc ctgtcagatt gctctagcta 4560
ggacttgcag tattgtgttg cataactgta gtgaaagtag tcatccttgt cttgttccag 4620
atcttaaaga aaaggctttc agtttttcccc cattcagtat gttactagct gtgagttgtc 4680
atatatggct tttattatat tgaggtctgt tccttgtata ctcagttttt ttagagtttt 4740
tatcatggaag ggatgttaaa cttatcaaat gctttttcag tatcaattga aatggtgata 4800
tggcttttgt cctttattct gttgatacga tgtattacat tgattgattt gtgtatgcat 4860
acctggaata cattccactt ggtcatgaag aatgatcttt ttaatatacct gttgaatgtg 4920
gtttgctagt atttcattga tgatatttgc ctcaatgttc atcagggata taggcctgta 4980
gttttctttt tttgatgtgt ctttgcctga ttttgatatc aggatattcc tggctttgta 5040
aaatgagttt ggaagtattc cctcctcctc tgttttttcag aacaatttga ataggactga 5100
tatttcttgt tcttttaaacg tttaattgtg gtaaattata cattacataa attttactgt 5160
tttaaccgct tttaagtgta tactcggttg cattagatac attcacattt ttgtgcaacc 5220
caaaactctg tacccattaa tcggtaactc cccattcctc cctacctctg gcccctggta 5280
accatcattc tacttttgt  ttctatgaat ttgaccactc taggtacctc atttaagtag 5340
aatcgtgtaa tgtttgtctt tttgattctg gcttatttca cttataatat ttcgagggtc 5400
atccaggttg tagtatgggt cagattttca ttccttttaa tgatgaataa tactcattat 5460
atgtatgtac cacacccttgg ttatccattc ctcagacaat ggacacttgg gttacttcta 5520
ccttttggat attggcaaat atttcatttc tctttgggtat atatttattt cttttgagta 5580
tttcttttgg gtatatatcc agaaatagaa ttgttggatc atacggtatt tcatttttta 5640
attttttagag gaatcaccat agtgttttcc attgcaggcg tgccattttg tatttctaga 5700
```

-continued

```
agcagtatac aggggcttca gtttctctac ctccttgcca aacttgctgt ttgtgtgtgt 5760
gtgtgtgtgt gtgtgtgtgt gtgtgtgtgt gtgtgtgata atagccaccc tgattggttt 5820
gaagtggtat ctcattgtgg tttggatttg cattttccta atgagtactg atattgagca 5880
tcttttcatg tgtttattga tcatttgtat attttcttg aagaattggc cattgaagtc 5940
ttgcccattt ttctccccca catagcttct catggctatt ttgcccattt ttgagtgggt 6000
tgactgtttt gttgttttg tcaaactttt ttgcatattc tggaaactaa tctctctctt 6060
tttctttttt ttttttttt tttttttga gatggagtct tgctctgttg cccaggctgg 6120
agtgcagtgg cacgatctca gctcactgca agctccaccc gctagcttca tgccattctc 6180
ccacctcagc ctccctagta gctgggacta caggcgcccg ccaccacacc cggctaattt 6240
tttgtatttt tagtagagat agggtttcac catgttagcc aggatggtct caatctcctg 6300
acctggtgat acacccgcct cggcctccca aagtgctgga attacaggct tgagccacca 6360
cgcctggcct tctggaagct aatctcttat cagatatatg acttgcaata tttatttcat 6420
ttcaggggtt gattgctttc tcactctgat tgtgcccttt gatgcacaga tattttgaat 6480
ttttcatgag tccagtttgt cagttctttc tattctatct gtgctttggc gtcatatcca 6540
tgaaagcact gtcaaaccct atgtcatgaa cattataccc aatgtttttt tctaagatat 6600
ttttatgttt tagttcttga gtttagagtt taggtctttg attcattttg agttaatttt 6660
tgtatatagt acaaattaag ggtccaattt tatattattt gaacatccag ttccccagc 6720
actatttgct gaaaagatgg acttactctt tgatacctg tcacctgccc accccagtgg 6780
acactagctg gtccatccaa ttgctgtcct ggggccttgt catgccactc ttccactttg 6840
aacccaagcc cacatcattg ctcccctctg ggatactgac cccactataa acttctctag 6900
ggctacaacc ttcctacccc ttgtgcctca tgaccacccc ctcccttgtc cccaccatgc 6960
ccatgatgag tcttttctca aggcagctcg ccttgcctcc atctcaccct cacctgtgca 7020
ccacagccac actggacatg ggtccctctg agcctgagtc ccttcccatt cccactgtcc 7080
cctctggcaa gaccttcctt ccaacactgc cttcatgctc ctcccttgcc cctgcagggc 7140
agcctctccc cttggcccct attccttag ggggcttgtg gccacccagt cctggcacct 7200
gacctacaag tttgccatct tcattcccc ttcttctgtt catcagcccc ctcctctatc 7260
ctcccaccct cacagttttc cttgtatatg aaatcttcgt tcttgtcctt ttgcccatgt 7320
gcatttcctg cctcctcagg gaggtcggga cagcagacct gtgtgttaaa catcaatgtg 7380
aagttatttc caggaagaag tttcacctgt gatttcctct tccccagagc cccacagtct 7440
tcgttacaac ctcatggtgc tgtcccagga tggatctgtg cagtcagggt ttctcgctga 7500
gggacatctg gatggtcagc ccttcctgcg ctatgacagg cagaaacgca gggcaaagcc 7560
ccagggacag tgggcagaag atgtcctggg agctgagacc tgggacacag agaccgagga 7620
cttgacagag aatgggcaag acctcaggag gaccctgact catatcaagg accagaaagg 7680
aggtgagagt cggcagggc aagagtaatg ggaggccttc tccaggaaag ttggagacag 7740
agagcaggga cctgtctctt cccgctggat ctggctgggg gtggggatga ggaatagggt 7800
cagggaggct cagcagggtg gtgagccgga actcagccca cacagggagg catggaggag 7860
ggccagggag gggtcgccgc tgggctgagt tcctcacttg ggtggaaagg tgatgggttc 7920
gggaatggag aagtcactgc tgggtggggg caggcttgca ttccctccag gagattaggg 7980
tctgtgagat ccatgaagac agcagcacca ggggctcccg gcatttctac tacaatgggg 8040
agctcttcct ctcccaaaac ctggagactc aagaatcgac agtgcccag tcctccagag 8100
ctcagacctt ggctatgaac gtcacaaatt tctggaagga agatgccatg aagaccaaga 8160
cacactatcg cgctatgcag gcagactgcc tgcagaaact acagcgatat ctgaaatccg 8220
gggtggccat caggagaaca ggtaccgacc ctggccaggg gctctactgt tcccgcaatt 8280
ctgctagagt tgcctcgcct cccagctctg tccagggaaa ccctccctgt gctatggatg 8340
caggcgtttc ctgttggcat attgtgtcct gatttgcctc tcctgttaga gccattggat 8400
aaagacagtg ggtctgggac tgaactgtcc agtgttgtaa tctgggaaag cagtgggccc 8460
tctgacagaa gcctgagcct ggggtgggag ttaggcagga gaggaagccc tcagggccag 8520
ggctgccccc tctgcctccc ggcctgccca tcccgagag ttccctcctg gccccatgac 8580
ccaggagtcc acccttgaca tccccctcct cagcatcaat gtgggatcc cagagcctga 8640
ggccacgtc ccaaggccca tcctcctgct agcctgagca cagggtgagg 8700
acagacttac agaaggtctg ggatctgtga gggattcagc cagagtgaga acagtggaga 8760
ggagcagccc tgttccctgc atctcccta gaggggagca gggcttcact ggctctgccc 8820
tttcttctcc agtgcccccc atggtgaatg tcacctgcag cgaggtctca gagggcaaca 8880
tcaccgtgac atgcagggct tccagcttct atcccgaa tatcacactg acctggcgtc 8940
aggatggggt atctttgagc cacaacaccc agcagtgggg ggatgtcctg cctgatggag 9000
atggaaccta ccagacctgg gtggccacca ggattcgcca aggagaggag cagaggttca 9060
cctgctacat ggaacacagc gggaatcacg gcactcaccc tgtgccctct ggtgagcctg 9120
gggtgaccct ggagagggtc aggccagggt aggaacagca gggacggctg tggctctctg 9180
cccagtgtat aacaagtccc ttttttcag ggaaggcgct ggtgcttcag agtcaacgtc 9240
cagactttcc atatgttct gctgctatgc catgttttgt tattattatt attctctgtg 9300
tcccttgttg caagaagaaa acatcagcgg cagagggtcc aggtgagaaa aggggacagt 9360
ttctggagat gggaaagctc cttttctagg agtagggtct cctcattgct cctgcccaga 9420
caagacgtag gtgacaaggc tgctggaaca ggggatggaa gctgggtat ttgggagggg 9480
aatgggagct gcatctccat ctacacccat aagtgcttct caagccaggg ctggggcaag 9540
gccttcgaat atccagctgt ggcctcctcc tgctgcaagt gaggagtggg cagcagggag 9600
ggctgtggca cctgtctctgt cccatccca gcctctctgt ctctcgggct cactagggtg 9660
cgtccaggtg gggtgagttg ggaatcacgt gctgattgct ggaggggctgg atgatcatgg 9720
tgtcagaggg aggaaatagt aaaggtggct gtgatctggg gagggccaga aactggagag 9780
gaatccaagg agaggcggtg cccaccgtg tgcctcctcc aggaggcact ttccaggttc 9840
ccaccacctg gcctcctga gtttccttgc agatgacaca gatgaataga taagcagatg 9900
tccctgggcc atttgaggag cgggcccag cccctcatca ggcagtttgt ggtccctgtt 9960
ttcatcctac ctccagcgtg ttttcttctg cagtccctga gggacacagt cccaggcgc 10020
catctctttg aggctttgtt ctgtgctctg tggccttacc ttgccctccc tgagccaatt 10080
tcccttttctc aaggtggtca ctgcctggta agtttggagt aagggacggt cagaagcatt 10140
tccccacag tcaggttgtt tgatggggga tgaaaagaga cagcagaagt tttgtgtttc 10200
tgcaaaaaca gaggcagtgc aggggacagt gagaggctgg ggtgtccagg agacctgagt 10260
ctggcggtag gggcgctggt ttctcatcct tgaacctaat tgcactgtca gtcggcccct 10320
catgcctgag cagatgggaa ggttcgtccc ctgccctgca gcaagagggc cctgtccagg 10380
aggcacccac agcaggggca gtgcaggtct gtggtcactc ctgctctcac ctgcggcgtc 10440
```

```
            tcccgtggag ggattgtcac ttctggttcc ctgtgggcag gaatggtttc ctcgtaggtc    10500
            actgggtttt tggccaggaa aagggtatga aattcatgtg ccagtttatc aaaattcctg    10560
            ctttcaatgt tgatgtccaa taaagatgtt cgtaatttca gctctataat cttaatagga    10620
            tttcctctaa tactgctgtt gtaaagcata ttaaataaaa caggaactca aatttggagc    10680
            cccctctcca gaagggtctg tgtggagatg gtggctgtgg cagcggcagt tcccaggtgc    10740
            agagggtggg cagaggcagc ctcaggctaa ggggtctccc ctactccacg tggagaaaag    10800
            tccttgtagg ttgcaagggc agtggcctgg gtgaatccc  tgctagggac agagcaggaa    10860
            ggcctcgcag cctcaccaag cagcagccct ggggtgaagt aagtggacca ggagtaagtg    10920
            gaccaggcag gagcagtagt gactcaacag caggtcacag gcctaggtgg gtgctgaagg    10980
            tcatgggagg ccaggcctcc tcgagcaagg tgggggtcc  cagggtcatg tcaggtgcag    11040
            atcctgtggc agccatgtct ttccatgctg ggcctgctgg gccccccagg cttcctgatg    11100
            gggtccccag ttaggagctg cctgctcagg gctgggaggg aggagtgct  gagctgcaga    11160
            tagagggcag ggcccacagt gggcagggcc tgccctggtg tgcaggtgcc tctgcaggag    11220
            aggagggcct ggggactgag agcaagggtc agggcctctc tttggggagg cctctcactg    11280
            taacaggact ggtcaggcct gagaggaggg cactgggttc cctcttgggt cttgtccttt    11340
            tgtcttgggg ccctttcact ccctgcacgg tgagtggtgg gcacaggaca ggggctgatg    11400
            ttgatggagt gatgggagag aactgacagg ggctgggaaa agcaaggagg gaggaagaaa    11460
            aaagtggggg cctcatcttc tctcagagaa agggtgaatc tgattttggg gcaactgaag    11520
            agagaaaagt ccttagggaa taaacacaac actgcaccca gtggagcatt taccgtttc     11580
            cctcttctcc agagcttgtg agcctgcagg tcctggatca acaccagtt  gggacaggag    11640
            accacaggga tgcagcacag ctgggatttc agcctctgat gtcagctact gggtccactg    11700
            gttccactga gggcgcctag actctacagc caggcggcca ggattcaact ccctgcctgg    11760
            atctcaccag cactttccct ctgtttcctg acctatgaaa cagaaaataa catcacttat    11820
            ttattgttgt tggatgctgc aaagtgttag taggtatgag gtgtttgctg ctctgccacg    11880
            tagagagcca gcaaagggat catgaccaac tcaacattcc attggaggct atatgatcaa    11940
            acagcaaatt gtttatcatg aatgcaggat gtgggcaaac tcacgactgc tcctgccaac    12000
            agaaggtttg ctgagggcat tcactccatg gtgctcattg gagttatcta ctgggtcatc    12060
            tagagcctat tgtttgagga atgcagtctt acaagcctac tctggaccca gcagctgact    12120
            ccttcttcca ccctccttct tgctatctcc tataccaata aatacgaagg gctgtggaag    12180
            atcagagccc ttgttcacga gaagcaagaa gcccctgac  cccttgttcc aaatatactc    12240
            ttttgtcttt ctcttttattc ccacgttcgc cctttgttca gtccaataca gggttgtggg    12300
            gcccttaaca gtgccatatt aattggtatc attatttctg ttgttttgt  ttttgttttt    12360
            gttttgtttt ttgagacaga gtctcactct gtcacccagg ctgcagttca ctgctgtgat    12420
            ctcagctcac tgcaacctct gcctccagg  ttcaagcact tctcgtacct cagactcccg    12480
            aatagctggg attacagaca ggcaccacca cacccagcta atttttgtat ttttgtaga     12540
            gacggggttt cgccaagttg accagcccag tttcaaactc ctgacctcag gtgatctgcc    12600
            tgccttggca tcccaaagtg ctgggattac aagaatgagc caccgtgcct ggcctatttt    12660
            attatattgt aatatatttt attatattag ccaccatgcc tgtcctattt tcttatgttt    12720
            taatatattt taatatatta catgtgcagt aattagatta tcatgggtga acttttatgag   12780
            tgagtatctt ggtgatgact cctcctgacc agcccaggac cagctttctt gtcaccttga    12840
            ggtcccctcg ccccgtcaca ccgttatgca ttactctgtg tctactatta tgtgtgcata    12900
            atttataccg taaatgttta ctctttaaat                                    12930
```

<210> SEQ ID NO 5
<211> LENGTH: 51
<212> TYPE: DNA
<213> ORGANISM: Homo Sapien
<220> FEATURE:
<221> NAME/KEY: misc_feature
<222> LOCATION: 26
<223> OTHER INFORMATION: n=A/G

<400> SEQUENCE: 5

```
     gtgggcagaa gatgtcctgg gagctnagac ctgggacaca gagaccgagg a          51
```

<210> SEQ ID NO 6
<211> LENGTH: 51
<212> TYPE: DNA
<213> ORGANISM: Homo Sapien
<220> FEATURE:
<221> NAME/KEY: misc_feature
<222> LOCATION: 26
<223> OTHER INFORMATION: n=A/G/C

<400> SEQUENCE: 6

```
     caggggctcc cggcatttct actacnatgg ggagctcttc ctctcccaaa a          51
```

<210> SEQ ID NO 7
<211> LENGTH: 101
<212> TYPE: DNA
<213> ORGANISM: Homo Sapien
<220> FEATURE:
<221> NAME/KEY: misc_feature
<222> LOCATION: 51

```
<223> OTHER INFORMATION: n = A or T

<400> SEQUENCE: 7
tttgtttctc cttaagtggc attttgactg tccattgcag cattctgatc ntaaaagaca    60
    tccactttgc taatgcacac gagattctct tagttgaagt a                       101

<210> SEQ ID NO 8
<211> LENGTH: 51
<212> TYPE: DNA
<213> ORGANISM: Homos sapien
<220> FEATURE:
<221> NAME/KEY: misc_feature
<222> LOCATION: 26
<223> OTHER INFORMATION: n=A/G

<400> SEQUENCE: 8
ctttggcaat tctatatggt gagctntaaa ggtgggctcc aggtagggat g              51

<210> SEQ ID NO 9
<211> LENGTH: 13
<212> TYPE: DNA
<213> ORGANISM: Artificial Sequence
<220> FEATURE:
<223> OTHER INFORMATION: homo sapien

<400> SEQUENCE: 9
cctgctccga ttc                                                       13

<210> SEQ ID NO 10
<211> LENGTH: 14
<212> TYPE: DNA
<213> ORGANISM: Artificial Sequence
<220> FEATURE:
<223> OTHER INFORMATION: homo sapien

<400> SEQUENCE: 10
ccctgctctg attc                                                      14

<210> SEQ ID NO 11
<211> LENGTH: 22
<212> TYPE: DNA
<213> ORGANISM: Artificial Sequence
<220> FEATURE:
<223> OTHER INFORMATION: homo sapien

<400> SEQUENCE: 11
atcagtcagt ggcccagaag ac                                             22

<210> SEQ ID NO 12
<211> LENGTH: 23
<212> TYPE: DNA
<213> ORGANISM: Artificial Sequence
<220> FEATURE:
<223> OTHER INFORMATION: homo sapien

<400> SEQUENCE: 12
gggacacaca agcatcaagg ata                                            23

<210> SEQ ID NO 13
<211> LENGTH: 720
<212> TYPE: DNA
<213> ORGANISM: Homo Sapiens
<220> FEATURE:
<221> NAME/KEY: misc_feature
<222> LOCATION: 452
<223> OTHER INFORMATION: n = C or G
```

```
<400> SEQUENCE: 13
ttcattcttc atcaaatcta agcataaaaa tagttttccc ctgggtcctt gggtcttcat  60
ttctgaaggc tcccatgtca cctaaaactt tgattaaata aatgtattat gcttttctct 120
tgttaatctg tcttttatta taggagtatt ggccataacc cttatgatgg gtcaggaagg 180
gatcacccct ttctgcccct acagaaataa tagctaagac tagtaaagca taaaaggcaa 240
aggggcaggt cctcaagtag agaagaacag gagaaatagc tcatacacac ccagaatgtt 300
acttacatgt ccctccatgt tacaccaaga cccctcaggg accttgtgcc tggggagaga 360
agtggtctgc cccatgcaac agtgggcttt accccgggtc accaccagcc ccagctccaa 420
cccctctaac actctccaag taaaatcaca tnagtagcag taataatatt tgaggtgaca 480
agttggtatt atctcaaact taggaaaagt gaataaagtc atctttagaa actgcttttt 540
ttaaacccctt gtaaccttgc aagctaagtg aaaatgggct catgtatgag aatgttcgtg 600
ttagacattt tttgggttcg acaaaactac gaaacaaacc aatccccatc acagatttat 660
tagaatatat tgatacaata gaatattaca tcatattttt tttaaaaaca ttactggtac 720
```

US 7,550,261 B2

METHOD OF SCREENING FOR DRUG HYPERSENSITIVITY REACTION

CROSS REFERENCE TO RELATED APPLICATIONS

This application claims priority from U.S. Provisional Application No. 60/314,026 filed Aug. 21, 2001 and U.S. Provisional Application No. 60/336,850 filed Oct. 30, 2001, and U.S. Provisional Application No. 60/358,302 filed 20 Feb. 2002.

BACKGROUND

Hypersensitivity reactions (HSR) are unexpected, immune (allergy)-like reactions that occur in a minority of patients treated with antiretroviral therapy. No single symptom or laboratory test has been found to predict or diagnose such events. Common symptoms, which appear in combinations, include fever, rash, gastrointestinal reactions, severe fatigue, and respiratory symptoms. Such hypersensitivity reactions constitute a distinct clinical entity and are not the simple rashes (mild rashes without systemic symptoms) that are common reactions to many drugs. Hypersensitivity reactions resolve on discontinuation of the causative drug, but return on reinitiation. The exact mechanism of hypersensitivity reactions is unknown.

Antiretroviral therapy has been demonstrated to be effective in the treatment of individuals infected with Human Immunodeficiency Virus (HIV) or diagnosed with Acquired Immune Deficiency Syndrome (AIDS). Therapy with combinations of antiretroviral agents can prolong survival and decrease the risk of complications of HIV-1 infection. Adverse reactions may occur with any antiretroviral agent, some with the potential to cause severe morbidity and mortality. (See e.g., Samuel et al., Antiretroviral Therapy 2000, Arch. Pharm. Res. 23:425 (2000); Carr et al., Lancet 356: 1423 (2000)). Common, and usually less severe, adverse reactions include nausea, headache, fatigue, diarrhea and non-severe skin rashes. Less common but sometimes severe adverse reactions to antiretroviral agents include severe skin rashes, pancreatitis, lactic acidosis, and hypersensitivity reactions.

Hypersensitivity reactions to abacavir (Ziagen) have been reported to occur among approximately 5% of patients who receive this agent alone or in combination with other antiretroviral agents (note that Ziagen is indicated for the treatment of HIV-1 infection in combination with other antiretroviral agents). Discontinuation of abacavir results in resolution of the symptoms of the hypersensitivity reaction. Continued administration of abacavir in the face of an ongoing reaction or reinstitution of abacavir in patients with a prior history of a reaction may result in a sudden, severe, and potentially fatal reaction.

A screening test to identify subjects at increased risk for a hypersensitivity reaction to a pharmaceutical compound would be useful in clinical medicine.

SUMMARY OF THE INVENTION

A first aspect of the present invention is a method of identifying genotypes that confer a increased or decreased risk for a hypersensitivity reaction to abacavir in human subjects. In a population of test subjects, each subject is genotyped for polymorphisms in a candidate gene, such as the TNFalpha (TNFα) gene, MICA, MICB, and/or HLA genes. A therapeutic regime of abacavir is administered to each subject (either prior to, concomitant with, or after genotyping of the subject), and test subjects that exhibit (or exhibited) clinical signs of a hypersensitivity reaction to abacavir are identified. The genotypes of the test subjects at polymorphic sites in the candidate genes are correlated with the occurrence of clinical signs of hypersensitivity reaction, to determine which genotypes are associated with an increased or decreased risk of hypersensitivity reaction (compared to other genotypes or to a general population that has not been stratified by genotype).

A further aspect of the present invention is a method of determining whether an individual is at increased risk of experiencing a hypersensitivity reaction to abacavir, by determining whether the individual has a genotype that is associated with an increased risk of hypersensitivity reaction, compared to the risk in subjects with alternate genotypes.

A further aspect of the present invention is a method of determining whether an individual is at decreased risk of experiencing a hypersensitivity reaction to abacavir, by determining whether the individual has a genotype that is associated with a decreased risk of hypersensitivity reaction, compared to the risk in subjects with alternate genotypes.

A further aspect of the present invention is a method of screening a human subject as an aid in assessing suitability to abacavir administration, by determining whether the subject has a TNFα genotype that has been associated with an increased risk of hypersensitivity reaction to abacavir compared to the risk in subjects with alternate TNFα genotypes. The presence of such a TNFα genotype indicates the subject is at increased risk for a hypersensitivity reaction to abacavir.

A further aspect of the present invention is a method of screening a human subject as an aid in assessing suitability to abacavir administration, by determining whether the subject has an HLA genotype that has been associated with an increased risk of hypersensitivity reaction to abacavir compared to the risk in subjects with alternate HLA genotypes. The presence of such an HLA genotype indicates the subject is at increased risk for hypersensitivity reaction to abacavir.

A further aspect of the present invention is a method of treating a human subject with abacavir, by first genotyping the subject to detect the presence or absence of the HLA-B57 allele, and then administering abacavir if the HLA-B57 allele is not detected.

A further aspect of the present invention is a method of screening a human subject as an aid in predicting the subject's risk of experiencing a hypersensitivity reaction to a therapeutic regime of abacavir, by genotyping a sample of DNA from the subject to determine the presence of a polymorphism in the TNFα gene, where the polymorphism has previously been associated with an increased risk of abacavir HSR compared to the risk of HSR associated with alternate TNFα polymorphisms. Detecting the presence of a TNFα genotype that has been associated with an increased incidence of hypersensitivity reaction to abacavir (compared to the incidence of abacavir HSR associated with other TNFα genotypes) indicates that the subject is at an increased risk of a hypersensitivity reaction to abacavir.

A further aspect of the present invention is a method of screening a human subject as an aid in predicting the subject's risk of experiencing a hypersensitivity reaction to a therapeutic regime of abacavir, by genotyping a sample of DNA from the subject to determine the presence of a polymorphism in an HLA gene, where the polymorphism has previously been associated with an increased risk of abacavir HSR compared to the risk of HSR associated with alternate polymorphisms. The presence of an HLA genotype that has been associated with an increased incidence of hypersensitivity reaction to abacavir (compared to the incidence of abacavir HSR associated with other HLA genotypes) indicates that the subject is at an increased risk of a hypersensitivity reaction to abacavir.

A further aspect of the present invention is a method of identifying human genotypes associated with an increased risk for a hypersensitivity reaction to abacavir, by genotyping each member of a population of test subjects for at least one polymorphism in the TNFα gene, administering a therapeutic regime of abacavir to each test subject, and identifying test subjects that exhibit clinical signs of a hypersensitivity reaction to abacavir. Correlating TNFα genotypes with the occurrence of clinical signs of hypersensitivity reaction, will determine which genotypes are associated with an increased risk of hypersensitivity reaction to abacavir (compared to the other detected genotypes).

A further aspect of the present invention is a method of identifying human genotypes associated with an increased risk for a hypersensitivity reaction to abacavir, by genotyping each member of a population of test subjects for at least one polymorphism in an HLA gene, administering a therapeutic regime of abacavir to each test subject, and identifying test subjects that exhibit clinical signs of a hypersensitivity reaction to abacavir. Correlating HLA genotypes with the occurrence of clinical signs of hypersensitivity reaction, will determine which genotypes are associated with an increased risk of hypersensitivity reaction to abacavir (compared to the other detected genotypes).

A further aspect of the present invention is a method of administering or prescribing abacavir to reduce the incidence of abacavir hypersensitivity reaction. The method comprises selecting, based on genotype status, a treatment population from a larger starting population of subjects who have a condition suitable for treatment with abacavir. The treatment population is selected to increase the percentage of subjects in the treatment population who have a genotype that has been associated with reduced risk of abacavir hypersensitivity reaction (the increased percentage of subjects in the treatment population is relative to the percentage of subjects in the starting population). Alternatively, the treatment population is selected to decrease the percentage of subjects in the treatment population who have a genotype that has been associated with increased risk of abacavir hypersensitivity reaction. Abacavir is then administered to the selected treatment population, thereby reducing the incidence of abacavir HSR in the treated population compared to the incidence that would have been expected to occur had abacavir been administered to the larger starting population. The 'selection' may occur by any suitable process as will be apparent to those skilled in the art. Examples of suitable selection methods include genetically screening starting population subjects, or otherwise classifying subjects by genotype (e.g., where a subject's genotype is known, genetic testing need not be repeated); or otherwise regulating access to abacavir to decrease the number of subjects in the treatment population who have genotypes that have been associated with an increased risk of abacavir HSR. One such genotype is the HLA-B57 allele, where the treatment population would be selected to minimize the occurrence of the HLA-B57 allele in the treatment population. Alternatively, the genotype of interest may be the TNF G(-237)A polymorphism, where the treatment population is selected to minimize the occurrence of the A allele.

DETAILED DISCUSSION

Anti-retroviral therapy in HIV-infected patients often comprises the use of multiple types of antiretroviral agents, including protease inhibitors, non-nucleoside reverse transcriptase inhibitors (NNRTI) and nucleoside reverse transcriptase inhibitors (NRTI). Abacavir is a synthetic purine nucleoside analogue that is commercially available as abacavir sulfate (ZIAGEN®; GlaxoSmithKline), and that is used in combination with other antiretroviral agents to treat HIV-infected subjects. Abacavir is an inhibitor (NRTI) of the HIV-1 reverse transcriptase that contains an unsaturated cyclopentene ring in place of the 2'deoxyriboside of natural deoxynucleosides, and contains a cyclopropylamino group. The chemical name of abacavir sulfate is (cis)-4-[2-amino-6-(cyclopropylamino)-9H-purin-9-yl]-2-cyclopentene-1-methanol sulfate (salt) (2:1).

Hypersensitivity reactions are idiosyncratic events of a presumed immunologic nature that occur with a broad range of pharmacological compounds. In the context of abacavir administration, hypersensitivity reactions to abacavir can be serious and progress to become life-threatening (Clay et al., Ann Pharmacotherapy 34(2):247 (2000); Staszewski et al., AIDS 12:F197 (1998)). In clinical trials, hypersensitivity to abacavir has occurred among approximately 5% of subjects.

Signs and symptoms of a hypersensitivity reaction to abacavir include (but are not limited to) fever, skin rash, fatigue, gastrointestinal symptoms (including nausea, vomiting, diarrhea, abdominal pain), and respiratory symptoms (including pharyngitis, dyspnea and cough). Additional signs and symptoms include malaise, lethargy, myalgia, myolysis, arthralgia, edema, headache and paresthesia. Physical findings include lymphadenopathy, mucous membrane lesions (conjunctivitis and mouth ulcerations). The rash associated with hypersensitivity reaction usually appears maculopapular or urticarial, but the appearance may be variable; up to 30% of hypersensitivity reactions have occurred without rash. Laboratory abnormalities include elevated liver function tests, increased creatine phosphokinase or creatinine, and lymphopenia. See Package Insert, Ziagen (abacavir sulfate), Glaxo Wellcome, Research Triangle Park, N.C. (1998); Clay et al., Management Protocol for Abacavir-related Hypersensitivity Reaction, Ann. Pharmacotherapy 34(2):247 (2000). Clay et al. state that the presence of rash alone does not warrant discontinuation of abacavir unless other systemic symptoms of hypersensitivity reaction occur.

TNFalpha

The immunologic effector molecule Tumor Necrosis Factor alpha (TNFα) is known to be polymorphic, and a number of polymorphisms have been reported in the TNFα promoter region. Some reports indicate that such promoter polymorphisms influence immunologic disease (Bouma et al., Scand. J. Immunol. 43:456 (1996); Allen et al., Mol. Immunology 36:1017 (1999)), whereas others suggest that observed associations between TNFα polymorphisms and disease occurrence are not due to functional effects of TNFα, but due to the linkage disequilibrium of TNFα with selectable HLA alleles (Uglialoro et al., Tissue Antigens, 52:359 (1998)). A list of TNFα promoter polymorphisms is provided by Allen et al., Mol. Immunology 36:1017 (1999). The numbering of TNFα polymorphisms has varied among authors due to the variation in sequences reported for TNFα promoter region; numbering herein refers to the following consensus sequence provided in Allen et al. (1999):

```
GGGGAAGCAA AGGAGAAGCT GAGAAGATGA AGGAAAAGTC AGGGTCTGGA GGGGCGGGGG  -1000   (SEQ ID NO:1)

TCAGGGAGCT CCTGGGAGAT ATGGCCACAT GTAGCGGCTC TGAGGAATGG GTTACAGGAG  -940

ACCTCTGGGG AGATGTGACC ACAGCAATGG GTAGGAGAAT GTCCAGGGCT ATGGAAGTCG  -880

AGTAT-GGGG ACCCCCCCTT AACGAAGACA GGGCCATGTA GAGGGCCCCA GGGAGTGAAA  -820

GAGCCTCCAG GACCTCCAGG TATGGAATAC AGGGGACGTT TAAGAAGATA TGGCCACACA  -760

CTGGGGCCCT GAGAAGTGAG AGCTTCATGA AAAAAATCAG GGACCCCAGA GTTCCTTGGA  -700

AGCCAAGACT GAAACCAGCA TTATGAGTCT CCGGGTCAGA ATGAAAGAAG AGGGCCTGCC  -640

CCAGTGGGGT CTGTGAATTC CCGGGGGTGA TTTCACTCCC CGGGGCTGTC CCAGGCTTGT  -580

CCCTGCTACC CCCACCCAGC CTTTCCTGAG GCCTCAAGCC TGCCACCAAG CCCCCAGCTC  -520

CTTCTCCCCG CAGGGACCCA AACACAGGCC TCAGGACTCA ACACAGCTTT TCCCTCCAAC  -460

CCCGTTTTCT CTCCCTCAA- GGACTCAGCT TTCTGAAGCC CCTCCCAGTT CTAGTTCTAT  -400

CTTTTTCCTG CATCCTGTCT GGAAGTTAGA AGGAAACAGA CCACAGACCT GGTCCCCAAA  -340

AGAAATGGAG GCAATAGGTT TTGAGGGGCA TGGGGACGGG GTTCAGCCTC CAGGGTCCTA  -280

CACACAAATC AGTCAGTGGC CCAGAAGACC CCCCTCGGAA TCGGAGCAGG GAGGATGGGG  -220

AGTGTGAGGG GTATCCTTGA TGCTTGTGTG TCCCCAACTT TCCAAATCCC CGCCCCCGCG  -160

ATGGAGAAGA AACCGAGACA GAAGGTGCAG GGCCCACTAC CGCTTCCTCC AGATGAGCTC  -100

ATGGGTTTCT CCACCAAGGA AGTTTTCCGC TGGTTGAATG ATTCTTTCCC CGCCCTCCTC  -40

TCGCCCCAGG GACATATAAA GGCAGTTGTT GGCACACCCA GCCAGCAGAC GCTCCCTCAG  +21

CAAGGACAGC AGAGGACCAG CTAAGAGGGA GAGAAGCAAC TGCAGACCCC CCC-TGAAAA  +81

CAACCCTCAG ACGCCACATC CCCTGACAAG CTGCCAGGCA GGTTCT
```

The transcription start site (+1) is indicated by bold underlined type; the G(-237)A and G(-308)A polymorphisms are indicated by bold, double underlined type. Due to variation in reported sequences and numbering, the G(-237)A polymorphism has also been referred to as G-238A, and the G(-308)A polymorphism is located at the -307 position on the above sequence. A further polymorphism, C(-5,100)G, investigated in the present research was an C/G polymorphism in the 5' untranslated region of TNFα:

```
TTCATTCTTC ATCAAATCTA AGCATAAAAA     (SEQ ID NO:13)

TAGTTTTCCC CTGGGTCCTT GGGTCTTCAT

TTCTGAAGGC TCCCATGTCA CCTAAAACTT

TGATTAAATA AATGTATTAT GCTTTTCTCT

TGTTAATCTG TCTTTTATTA TAGGAGTATT

GGCCATAACC CTTATGATGG GTCAGGAAGG

GATCACCCCT TTCTGCCCCT ACAGAAATAA

TAGCTAAGAC TAGTAAAGCA TAAAAGGCAA

AGGGGCAGGT CCTCAAGTAG AGAAGAACAG

GAGAAATAGC TCATACACAC CCAGAATGTT

ACTTACATGT CCCTCCATGT TACACCAAGA

CCCCTCAGGG ACCTTGTGCC TGGGGAGAGA

AGTGGTCTGC CCCATGCAAC AGTGGGCTTT
```

-continued

```
ACCCCGGGTC ACCACCAGCC CCAGCTCCAA

CCCCTCTAAC ACTCTCCAAG TAAAATCACA

TNAGTAGCAG TAATAATATT TGAGGTGACA

AGTTGGTATT ATCTCAAACT TAGGAAAAGT

GAATAAAGTC ATCTTTAGAA ACTGCTTTTT

TTAAACCCTT GTAACCTTGC AAGCTAAGTG

AAAATGGGCT CATGTATGAG AATGTTCGTG

TTAGACATTT TTTGGGTTCG ACAAAACTAC

GAAACAAACC AATCCCCATC ACAGATTTAT

TAGAATATAT TGATACAATA GAATATTACA

TCATATTTTT TTTAAAAACA TTACTGGTAC
N = C/G
```

Allen et al. (supra) note that a number of the TNFα promoter polymorphisms observed to date are G/A polymorphisms clustered in the region of -375 to -162 bp; that some of these polymorphisms lie within a common motif; and suggest that the motif could be a consensus binding site for a transcriptional regulator or might influence DNA structure. The G/A polymorphism at -237 has been reported to affect DNA curvature (D'Alfonso et al., Immunogenetics 39:150 (1994)). Huizinga et al. (J. Neuroimmunology 72:149, 1997) reported significantly less TNFα production by LPS-stimulated cells from individuals heterozygous (G/A) at -237

(compared to G/G individuals); however, a separate study did not observe these effects (Pociot et al., Scand. J. Immunol. 42:501, 1995). The G(-237)A polymorphism has also been reported to affect autoimmune disease (Brinkman et al., Br. J. Rheumatol. 36:516 1997 (rheumatoid arthritis); Huizinga et al., J. Neuroimmunology 72:149 1997 (multiple sclerosis); Vinasco et al., Tissue Antigens, 49:74 1997 (rheumatoid arthritis)) and infectious disease (Hohler et al., Clin. Exp. Immunol. 111:579 1998 (hepatitis B); Hohler et al., J. Med. Virol. 54:173 1998 (hepatitis c)).

As is well known genetics, nucleotide and amino acid sequences obtained from different sources for the same gene may vary both in the numbering scheme and in the precise sequence. Such differences may be due to inherent sequence variability within the gene and/or to sequencing errors. Accordingly, reference herein to a particular polymorphic site by number (e.g., TNFα G-238A) will be understood by those of skill in the art to include those polymorphic sites that correspond in sequence and location within the gene, even where different numbering/nomenclature schemes are used to describe them.

HLA

The HLA complex of humans (major histocompatibility complex or MHC) is a cluster of linked genes located on chromosome 6. (The TNFα and HLA B loci are in proximity on chromosome 6). The HLA complex is classically divided into three regions: class I, II, and III regions (Klein J. In: Gotze D, ed. The Major Histocompatibility System in Man and Animals, New York: Springer-Verlag, 1976: 339–378). Class I HLAs comprise the transmembrane protein (heavy chain) and a molecule of beta-2 microglobulin. The class I transmembrane proteins are encoded by the HLA-A, HLA-B and HLA-C loci. The function of class I HLA molecules is to present antigenic peptides (including viral protein antigens) to T cells. Three isoforms of class II MHC molecules, denoted HLA-DR, -DQ, and -DP are recognized. The MHC class II molecules are heterodimers composed of an alpha chain and a beta chain; different alpha- and beta-chains are encoded by subsets of A genes and B genes, respectively. Various HLA-DR haplotypes have been recognized, and differ in the organization and number of DRB genes present on each DR haplotype; multiple DRB genes have been described. Bodmer et al., Eur. J. Immunogenetics 24:105 (1997); Andersson, Frontiers in Bioscience 3:739 (1998).

The MHC exhibits high polymorphism; more than 200 genotypical alleles of HLA-B have been reported. See e.g., Schreuder et al., Human Immunology 60: 1157–1181 (1999); Bodmer et al., European Journal of Immunogenetics 26: 81–116 (1999). Despite the number of alleles at the HLA-A, HLA-B and HLA-C loci, the number of haplotypes observed in populations is smaller than mathematically expected. Certain alleles tend to occur together on the same haplotype, rather than randomly segregating. This is called linkage disequilibrium (LD) and may be quantitated by methods as are known in the art (see, e.g., Devlin and Risch, Genomics 29:311 (1995); BS Weir, Genetic Data Analysis II, Sinauer Associates, Sunderland, Md. (1996)).

The products encoded by the polymorphic HLA loci are commonly typed by serological methods for transplant and transfusion histocompatibility testing, and blood component therapy. Serological typing is based on reactions between characterized sera and the HLA gene products. Known techniques for histocompatibility testing include microlymphocytotoxicity and flow cytometry. Standard microlymphocytotoxicity for HLA antigen typing determines the HLA antigen profile of a subject's lymphocytes, using a panel of well characterized HLA antisera. The HLA-B57 allele is well characterized, and serologic methods of detecting HLA-B57 are known. See e.g., ASHI Laboratory Manual, Fourth Edition, American Society for Histocompatibility and Immunogenetics (2000); Hurley et al., Tissue Antigens 50:401 (1997).

More recently, methods for analysis of HLA polymorphisms at the genetic level have been developed. Non-serological HLA typing methods include the use of DNA restriction fragment length polymorphism (RFLP; see e.g., Erlich U.S. Pat. No. 4,582,788 (1986)), or labelled oligonucleotides, to identify specific HLA DNA sequences. Such methods may detect polymorphisms located in either the coding or noncoding sequence of the genome. See e.g., Bidwell et al, Immunology Today 9:18 (1988), Angelini et al., Proc. Natl. Acad. Sci. USA, 83:4489 (1986); Scharf et al., Science, 233:1076 (1986); Cox et al., Am. J. Hum. Gen., 43:954 (1988); Tiercy et al., Proc. Natl. Acad. Sci. USA 85:198 (1988); and Tiercy et al., Hum. Immunol. 24:1 (1989). The polymerase chain reaction (PCR) process (see U.S. Pat. No. 4,683,202, 1987) allows amplification of genomic DNA and is now used for HLA typing procedures. See Saiki et al., Nature 324:163 (1986); Bugawan et al., J. Immunol. 141:4024 (1988); Gyllensten et al., Proc. Natl. Acad. Sci. USA, 85:7652 (1988). See also e.g., Ennis et al., PNAS USA 87:2833 (1990); Petersdorf et al., Tissue Antigens 46: 77 (1995); Girdlestone et al., Nucleic Acids Research 18:6702 (1990); Marcos et al., Tissue Antigens 50:665 (1997); Steiner et al., Tissue Antigens 57:481 (2001); Madrigal et al., J. Immunology 149:3411 (1992).

As used herein, 'genotyping' an HLA locus refers to methods that identify the presence or absence of a particular allele, or nucleic acid or amino acid sequence; sequence variations may be detected directly (by sequencing) or indirectly (e.g., by restriction fragment length polymorphism analysis, or detection of the hybridization of a probe of known sequence, or reference strand conformation polymorphism). HLA alleles may be detected serologically, as is known in the art.

Distinct HLA alleles have been associated with an increased or decreased risk of progression of HIV disease. The HLA-B57 and HLA-B14 alleles have been associated with non-progressive HIV infection, whereas HLA-A29 and HLA-B22 have been associated with rapid progression. Goulder et al., J. Virology 74:5291 (2000); Hendel et al., J. Immunology 162:6942 (1999). Carrington et al., reported that the allele frequency of HLA-B57 in HIV infected patient cohorts is 4.40% in Caucasians and 5.7% in African Americans. Carrington et al., Science, 283:1748 (1999).

MICA and MICB

The MHC (HLA) class I chain-related gene A (MICA) and MHC (HLA) class I chain-related gene B (MICB) belong to a multicopy gene family located in the major histocompatibility complex (MHC) class I region near the HLA-B gene. They are located within a linkage region on chromosome 6p around HLA-B and TNFalpha. The encoded MHC class I molecules are induced by stress factors such as infection and heat shock, and are expressed on gastrointestinal epithelium.

MICA is reported as highly polymorphic. The occurrence of MICA single nucleotide polymorphisms in various ethnic groups is reported by Powell et al., Mutation Research 432:47 (2001). Polymorphisms in MICA have been reported to be associated with various diseases, although in some cases the association was attributable to linkage disequilibrium with HLA genes. See, e.g., Salvarani et al., J Rheumatol 28:1867 (2001); Gonzalez et al., Hum Immunol 62:632 (2001); Seki et al., Tissue Antigens 58:71 (2001).

Various polymorphic forms of MICB have been reported (see, e.g., Visser et al., Tissue Antigens 51:649 (1998); Kimura et al., Hum Immunol 59:500 (1998); Ando et al., Immunogenetics 46:499 (1997); Fischer et al., Eur J Immunogenet 26:399 (1999)).

A partial sequence for homo sapiens MICA gene, including exons 2 and 3, is provided below (GenBank reference AJ295250).

```
exon 2  <1 . . . 255
exon 3  530 . . . 817
     1 agccccacag tcttcgttat aacctcacgg   (SEQ ID NO:2)
       tgctgtccgg ggatggatct gtgcagtcag 61 ggtttctcgc tgagggacat ctggatggtc
       agcccttcct gcgctgtgac aggcagaaat 121 gcagggcaaa gccccaggga cagtgggcag
       aagatgtcct gggaaataag acatgggaca 181 gagagaccag ggacttgaca gggaacggaa
       aggacctcag gatgaccctg gctcatatca 241 aggaccagaa agaaggtgag agtcggcagg
       ggcaagagtg actggagagg ccttttccag 301 aaaagttagg ggcagagagc agggacctgt
       atctacccac tggatctggc tcaggctggg 361 ggtgaggaat ggggtcagt ggaactcagc
       agggaggtga gccggcactc agcccacaca 421 gggaggcatg gaggagggcc agggaggcgt
       accccctggg ctgagttcct cacttgggtg 481 gaaaggtgat gggttcggga atggagaagt
       cactgctggg tgggggcagg cttgcattcc 541 ctccaggaga ttagggtctg tgagatccat
       gaagacaaca gcaccaggag ctcccagcat 601 ttctactacg atggggagct cttcctctcc
       caaaacctgg agactgagga atggacaatg 661 ccccagtcct ccagagctca gaccttggcc
       atgaacgtca ggaatttctt gaaggaagat 721 gccatgaaga ccaagacaca ctatcacgct
       atgcatgcag actgcctgca ggaactacgg 781 cgatatctaa aatccggcgt agtcctgagg
                                  agaacag
```

Various MICA polymorphisms were investigated in the present study. The MICA polymorphisms in exon 2 (T/G; rs1063630 in the National Center for Biotechnology Information SNP database (dbSNP)) and exon 3 (A/G; rs1051792) are shown above in bold, double-underlined type. An additional MICA polymorphism investigated in the present study (rs1052416) was located approximately −9,263 bases 5' to the transcription start site:

```
MICA (-9,263)                          (SEQ ID NO:3)
CACTGGGTTTGTTGCAGTAAGCCACNTCGAATGTTGCTGTAGAATTAAAGT
N = A/G
```

A complete cds for the human MICB gene is provided at SEQ ID NO:4 (GenBank accession U65416). The MICB polymorphisms investigated in the present study included one in exon 2 (rs1065075) and one in exon 3 (rs1051788):

```
MICB-(rs1065075)  N = A/G               SEQ ID NO:5
GTGGGCAGAAGATGTCCTGGGAGCTNAGACCTGGGACACAGAGACCGAGGA
```

```
MICB (rs1051788)  N = A/G               SEQ ID NO:6
CAGGGGCTCCCGGCATTTCTACTACNATGGGGAGCTCTTCCTCTCCCAAAA
```

ATP Dependent RNA Helicase p47

The protein encoded by this gene is a member a family of ATP-dependent RNA helicases, and is also known as HLA-B associated transcript 1 (BAT1) (see, e.g., GenBank Accession No. AF029061). A cluster of genes known as BAT1-BAT5 has been localized near the TNF and TNF genes. Various polymorphisms have been identified in ATP dependent RNA Helicase p47, including:

```
N = A/T                                 (SEQ ID NO:7)
TTTGTTTCTCCTTAAGTGGCATTTTGACTGTCCATTGCAGCATTCTGATC
NTAAAAGACATCCACTTTGCTAATGCACACGAGATTCTCTTAGTTGAAGT
A
```

```
RS929138;  N = C/T                      (SEQ ID NO:8)
CTTTGGCAATTCTATATGGTGAGCTNTAAAGGTGGGCTCCAGGTAGGGAT
G
```

Definitions

As is well known genetics, nucleotide and amino acid sequences obtained from different sources for the same gene may vary both in the numbering scheme and in the precise sequence. Such differences may be due to numbering schemes, inherent sequence variability within the gene, and/or to sequencing errors. Accordingly, reference herein to a particular polymorphic site by number (e.g., TNFα G-238A) will be understood by those of skill in the art to include those polymorphic sites that correspond in sequence and location within the gene, even where different numbering/nomenclature schemes are used to describe them.

As used herein, a drug "hypersensitivity reaction" (HSR) refers to the development of an immune-like response to a drug molecule or a metabolite of the drug. This response is typically characterized by multiple symptoms and is consistent with the clinical descriptions of such syndromes (Knowles et al., Lancet. 356:1587 (2000); Carr et al., Lancet. 356:1423, (2000)). The immunologic reaction shares features of, but is not necessarily identical to, the types present in the Gell and Coombs system. See Sullivan T J: Drug allergy, In Middleton et al. (eds): *Allergy: Principles and Practice*, 4th Ed., St. Louis, Mosby, 1993, p. 1730. Abacavir HSR may be characterized by the occurrence of multiple or single symptoms, and clinical diagnosis of abacavir HSR or probable abacavir HSR can be made based on the presence of one or more clinical signs and symptoms, physical findings, with or without laboratory abnormalities, as will be apparent to one skilled in the art.

Administering abacavir to a subject (or "treating" a subject with abacavir) comprises methods and routes of administration as are known in the art. Recommended therapeutic regimes (dosing amounts and schedules, plasma concentrations) of abacavir are known in the art. As used herein, administration of abacavir is not limited to the treatment of HIV-related disease or AIDS, but includes its medical use for other conditions amenable to treatment with abacavir.

As used herein, administration of a pharmaceutical reverse transcriptase inhibitor to a subject comprises administration of an effective amount of the pharmaceutical agent to a subject in need thereof. The dose of a pharmaceutical agent can be determined according to methods known and accepted in the pharmaceutical arts, and can be determined by those skilled in the art. Reverse transcriptase inhibitors (NRTIs and NNRTIs) are known for the treatment of HIV disease and/or AIDS.

As used herein, the "HLA-B57 allele" refers to an HLA-B allele that is serologically characterizable as the HLA-B57 allele, as is known in the art. It will be recognized that serologically characterized HLA-B57 alleles comprise sequence variants which may be detected at the nucleic acid sequence level (e.g., HLA-B*5701, HLA-B*5702; see e.g. Schreuder et al., Human Immunology 60: 1157–1181 (1999).

As used herein, "genotyping" a subject (or DNA sample) for a polymorphic allele of a gene(s) means detecting which allelic or polymorphic form(s) of the gene(s) are present in a subject (or a sample). As is well known in the art, an individual may be heterozygous or homozygous for a particular allele. More than two allelic forms may exist, thus there may be more than three possible genotypes. For purposes of the present invention, "genotyping" includes the determination of HLA alleles using suitable serologic techniques, as are known in the art. As used herein, an allele may be 'detected' when other possible allelic variants have been ruled out; e.g., where a specified nucleic acid position is found to be neither adenine (A), thymine (T) or cytosine (C), it can be concluded that guanine (G) is present at that position (i.e., G is 'detected').

As used herein, a "genetic subset" of a population consists of those members of the population having a particular genotype. In the case of a biallelic polymorphism, a population can potentially be divided into three subsets: homozygous for allele 1 (1,1), heterozygous (1,2), and homozygous for allele 2 (2,2). A 'population' of subjects may be defined using various criteria, e.g., individuals being treated with abacavir, HIV-infected individuals, individuals of a particular ethnic background. It is known that the frequency of a particular allele may differ among populations of different ethnic backgrounds. For example, the allele frequency of HLA-B57 has been reported as approximately 4% among Blacks and Caucasians (consequently about 8% of such a population carry at least one copy of the HLA-B57 allele), but among Japanese the frequency has been reported as 0.3%. Cao et al., Human Immunology 62:1009 (2001). The distribution of subtypes of HLA-B57 also varies by ethnicity, with >90% of HLA-B57 positive Caucasians reported as subtype HLA-B5701 compared to approximately 60% of African Americans. Williams et al., Human Immunology 62:645 (2001).

As used herein, a subject that is "predisposed to" or "at increased risk of" a particular phenotypic response based on genotyping will be more likely to display that phenotype than an individual with a different genotype at the target polymorphic locus (or loci). Where the phenotypic response is based on a multi-allelic polymorphism, or on the genotyping of more than one gene, the relative risk may differ among the multiple possible genotypes.

"Genetic testing" (also called genetic screening) as used herein refers to the testing of a biological sample from a subject to determine the subject's genotype; and may be utilized to determine if the subject's genotype comprises alleles that either cause, or increase susceptibility to, a particular phenotype (or that are in linkage disequilibrium with allele(s) causing or increasing susceptibility to that phenotype).

"Linkage disequilibrium" refers to the tendency of specific alleles at different genomic locations to occur together more frequently than would be expected by chance. Alleles at given loci are in complete equilibrium if the frequency of any particular set of alleles (or haplotype) is the product of their individual population frequencies A commonly used measure of linkage disequilibrium is r:

$$r = \frac{\hat{\Delta}_{AB}}{\sqrt{(\tilde{\pi}_A + \hat{D}_A)(\tilde{\pi}_B + \hat{D}_B)}}$$

where $\tilde{\pi}_A = \tilde{p}_A(1 - \tilde{p}_A), \tilde{\pi}_B = \tilde{p}_B(1 - \tilde{p}_B), \hat{D}_A = \tilde{P}_{AA} - \tilde{p}_A^2, \hat{D}_B = \tilde{P}_{BB} - \tilde{p}_B^2$ $\hat{\Delta}_{AB} = \frac{1}{n}n_{AB} - 2\tilde{p}_A\tilde{p}_B$ $nr^2$ has an approximate chi square distribution with 1 degree freedom for biallelic markers. Loci exhibiting an r such that $nr^2$ is greater than 3.84, corresponding to a significant chi-squared statistic at the 0.05 level, are considered to be in linkage disequilibrium (BS Weir 1996 Genetic Data Analysis II Sinauer Associates, Sunderland, Md.).

Alternatively, a normalized measure of linkage disequilibrium can be defined as:

$$D'_{AB} = \begin{cases} \frac{D_{AB}}{\min(p_A p_B, p_a p_b)}, D_{AB} < 0 \\ \frac{D_{AB}}{\min(p_A p_b, p_a p_B)}, D_{AB} > 0 \end{cases}$$

The value of the D' has a range of −1.0 to 1.0. When statistically significant absolute D' value for two markers is not less than 0.3 they are considered to be in linkage disequilibrium.

As used herein the phrase 'an HLA-B57 genotype' refers to a genotype that includes the HLA-B57 allele. An HLA-B57 genotype can be identified by detecting the presence of an HLA-B57 allele, or detecting a genetic marker known to be in linkage disequilibrium with HLA-B57.

As used herein, determination of a 'multilocus' genotype refers to the detection within an individual of the alleles present at more than one locus. A subject may be genetically screened to determine the presence or absence of both an HLA allele (e.g., the HLA-B57 allele) and a TNFα allele (e.g., at the TNFα G(-237)A locus).

As used herein, the process of detecting an allele or polymorphism includes but is not limited to serologic and genetic methods. The allele or polymorphism detected may be functionally involved in affecting an individual's phenotype, or it may be an allele or polymorphism that is in linkage disequilibrium with a functional polymorphism/allele. Polymorphisms/alleles are evidenced in the genomic DNA of a subject, but may also be detectable from RNA, cDNA or protein sequences transcribed or translated from this region, as will be apparent to one skilled in the art.

Alleles, polymorphisms or genetic markers that are 'associated' with HSR to a NRTI such as abacavir are over-represented in frequency in treated subjects experiencing HSR as compared to treated subjects who do not experience HSR, or as compared to the general population.

According to the present methods, subjects who are being treated with abacavir, or who are considering treatment with abacavir, can be screened as an aid in predicting their risk of experiencing a hypersensitivity reaction to abacavir. Screening comprises obtaining a biological sample from the subject and analyzing it to determine the genotype of the TNFα, and/or HLA genes, i.e., to determine the presence or absence of polymorphisms in one or both of these genes that are associated with an increased risk of abacavir HSR (compared to the risk associated with alternative polymorphisms).

The present inventors have established that a correlation exists between an individual's HLA genotype (particularly class I, and more particularly HLA-B), and/or TNFα genotype, and the risk of experiencing a hypersensitivity reaction to abacavir administration. Accordingly, a method of assessing an individual's relative risk of an abacavir HSR involves genotyping that individual at the TNFα gene or the HLA genes to determine whether the individual's genotype places them at increased risk of abacavir HSR. Individuals possessing a TNFα or HLA genotype that has been previously associated with an increased incidence of abacavir HSR (compared to the incidence of HSR in subjects with alternate genotypes) are at increased risk of HSR.

The present screening methods comprise genotyping a subject at HLA genes, particularly the HLA class I genes, more particularly the HLA-B gene, including to detect the presence or absence of the HLA-B57 allele (as defined herein).

The present screening methods also comprise genotyping a subject at the TNFα gene, and more particularly, detecting the genotype at the TNFα G(-237)A polymorphic site (as defined herein), where detection of an A allele indicates increased risk of hypersensitivity reaction, compared to detection of a G/G genotype.

In view of the present disclosure, it will be apparent to one skilled in the art how to determine additional TNFα and/or HLA genotypes that are associated with an increased risk of abacavir HSR. Various allelic forms of the TNFα and HLA genes are known, and methods of typing the TNFα and HLA genes are known in the art. As additional polymorphisms are detected in human TNFα and HLA genes, typing for such polymorphisms may be based on known methods. Accordingly, one may type a population of subjects who have received abacavir and correlate TNFα and/or HLA genotype with the occurrence of HSR. In an alternate method, one may genotype only those subjects who have experienced HSR and, where the prevalence of a TNFα or HLA allele is known in a matched control (non-HSR) population, determine whether the allele is over-represented in the HSR population, indicating that it is associated with HSR. As will be apparent to one skilled in the art, the detection of a TNFα or HLA allele may be accomplished by typing for genetic markers that are known to be in linkage disequilibrium with the target TNFα or HLA allele/polymorphism. Preferably such markers are in substantial linkage disequilibrium, more preferably the markers are in complete linkage disequilibrium.

The present invention also provides a method of assessing an individual's relative risk of experiencing HSR to abacavir by determining the genotype at both the TNFα and HLA genes, to determine whether the individual's genotype places them at increased risk of abacavir HSR. Those individuals possessing a combined TNFα/HLA genotype that is associated with an increased incidence of abacavir HSR (compared to the incidence of HSR in subjects with alternate genotypes) are at increased risk of HSR. In particular, the present methods may comprise detecting the allelic form of the TNFα G(-237)A polymorphism and the presence or absence of the HLA-B57 allele (and/or markers in linkage disequilibrium with these).

It will be apparent to those skilled in the art that, as multiple TNFα and HLA genotypes exist, the relative risk of abacavir HSR may vary among the multiple genotypes. E.g., in a multilocus screening method where more than two genotypes are found, relative risk may be determined to be highest for one genotype, lowest for another, and intermediate in others. 'Increased risk' may be as compared to the risk in a population that has not been stratified by genotype (a general population), or increased as compared to the risk expected in another defined genotype.

The presence of a particular predetermined genotype that is associated with an increased risk of HSR therefore indicates an increased likelihood that the individual will exhibit the associated phenotype (HSR reaction) relative to subjects with alternate genotypes. The genotype will rarely be absolutely predictive, i.e., where a population with a certain genotype displays a high incidence of an associated phenotype, not every individual with that genotype will display the phenotype. Likewise, some individuals with a different genotype may display the same phenotype. However, it will be apparent to those skilled in the art that genotyping a subject as described herein will be an aid in predicting a subject's risk of HSR to treatment with abacavir, and thus assist in treatment decisions. The present methods may further comprise administering abacavir to subjects after screening in subjects where the risk of HSR is deemed acceptable; the final treatment decision will be based on factors in addition to genetic testing (as will be readily apparent to one skilled in the art), including the subject's overall health status and expected treatment outcome.

It will be apparent to those skilled in the art that the present methods are also applicable where hypersensitivity reactions occur in response to synthetic nucleoside analogs other than abacavir, and particularly NRTIs. In particular, such compounds include purine nucleoside analogs, purine nucleoside analogs containing an unsaturated carbon ring in place of the 2'deoxyriboside of natural deoxynucleosides, and purine nucleoside analogs containing an unsaturated cyclopentene ring in place of the 2'deoxyriboside of natural deoxynucleosides. Further, the present methods are applicable where HSR occurs in response to NNRTIs, such as efavirenz (SUSTIVA™, Dupont Pharmaceuticals) and nevirapine (VIRAMUNE®, Boerhinger Ingelheim/Roxane).

According to the present methods, a compound (such as an NRTI or NNRTI) may be screened for variation in the incidence of HSR among genetic subpopulations of subjects. Such methods include administering the compound to a population of subjects, obtaining biological samples from the subjects (which may be done either prior to or after administration of the compound), genotyping polymorphic allelic sites in the TNFα gene and/or the class I HLA genes (particularly the HLA-B gene), and correlating the genotype of the subjects with their phenotypic response (e.g., the absence of hypersensitivity reaction versus the presence of confirmed or suspected hypersensitivity reaction). As will be apparent to those skilled in the art, due to the serious nature of HSR, administration of a pharmaceutical compound may need to be discontinued where a hypersensitivity reaction is suspected due to the presence of rash and/or other symptoms compatible with the clinical syndrome. Correlation of certain genotypes with an increased rate of HSR (where the HSR is either confirmed or clinically suspected), compared to the incidence of HSR in subjects with alternative genotypes, indicates that the incidence of HSR varies among genetic subpopulations.

Stated another way, the methods of the present invention may be used to determine the correlation of a polymorphic allele (such as those in TNFα and/or HLA alleles), with the incidence of hypersensitivity reaction to a pharmaceutical compound, particularly an NRTI. Subjects are stratified according to genotype and their response to the therapeutic agent is assessed (either prospectively or retrospectively) and compared among the genotypes. In this way, genotypes that are associated with an increased (or decreased) rate of HSR may be identified. The increase or decrease of HSR rates is in comparison to the rates among other genotypes, or to a population as a whole (i.e. the incidence in a population that is not stratified by genotype).

Polymorphic alleles may be detected by determining the DNA polynucleotide sequence, or by detecting the corresponding sequence in RNA transcripts from the polymorphic gene, or where the nucleic acid polymorphism results in a change in an encoded protein by detecting such amino acid sequence changes in encoded proteins; using any suitable technique as is known in the art. Polynucleotides utilized for typing are typically genomic DNA, or a polynucleotide fragment derived from a genomic polynucleotide sequence, such as in a library made using genomic material from the individual (e.g. a cDNA library). The polymorphism may be detected in a method that comprises contacting a polynucleotide or protein sample from an individual with a specific binding agent for the polymorphism and determining whether the agent binds to the polynucleotide or protein, where the binding indicates that the polymorphism is present. The binding agent may also bind to flanking nucleotides and amino acids on one or both sides of the polymorphism, for example at least 2, 5, 10, 15 or more flanking nucleotide or amino acids in total or on each side. In the case where the presence of the polymorphism is being determined in a polynucleotide it may be detected in the double stranded form, but is typically detected in the single stranded form.

The binding agent may be a polynucleotide (single or double stranded) typically with a length of at least 10 nucleotides, for example at least 15, 20, 30, or more nucleotides. A polynucleotide agent which is used in the method will generally bind to the polymorphism of interest, and the flanking sequence, in a sequence specific manner (e.g. hybridize in accordance with Watson-Crick base pairing) and thus typically has a sequence which is fully or partially complementary to the sequence of the polymorphism and flanking region. The binding agent may be a molecule that is structurally similar to polynucleotides that comprises units (such as purine or pyrimidine analogs, peptide nucleic acids, or RNA derivatives such as locked nucleic acids (LNA)) able to participate in Watson-Crick base pairing. The agent may be a protein, typically with a length of at least 10 amino acids, such as at least 20, 30, 50, or 100 or more amino acids. The agent may be an antibody (including a fragment of such an antibody that is capable of binding the polymorphism).

In one embodiment of the present methods a binding agent is used as a probe. The probe may be labeled or may be capable of being labeled indirectly. The detection of the label may be used to detect the presence of the probe on (bound to) the polynucleotide or protein of the individual. The binding of the probe to the polynucleotide or protein may be used to immobilize either the probe or the polynucleotide or protein (and thus to separate it from one composition or solution).

In another embodiment of the invention the polynucleotide or protein of the individual is immobilized on a solid support and then contacted with the probe. The presence of the probe immobilized to the solid support (via its binding to the polymorphism) is then detected, either directly by detecting a label on the probe or indirectly by contacting the probe with a moiety that binds the probe. In the case of detecting a polynucleotide polymorphism the solid support is generally made of nitrocellulose or nylon. In the case of a protein polymorphism the method may be based on an ELISA system.

The present methods may be based on an oligonucleotide ligation assay in which two oligonucleotide probes are used. These probes bind to adjacent areas on the polynucleotide which contains the polymorphism, allowing (after binding) the two probes to be ligated together by an appropriate ligase enzyme. However the two probes will only bind (in a manner which allows ligation) to a polynucleotide that contains the polymorphism, and therefore the detection of the ligated product may be used to determine the presence of the polymorphism.

In one embodiment the probe is used in a heteroduplex analysis based system to detect polymorphisms. In such a system when the probe is bound to a polynucleotide sequence containing the polymorphism, it forms a heteroduplex at the site where the polymorphism occurs (i.e. it does not form a double strand structure). Such a heteroduplex structure can be detected by the use of an enzyme that is single or double strand specific. Typically the probe is an RNA probe and the enzyme used is RNAse H that cleaves the heteroduplex region, thus allowing the polymorphism to be detected by means of the detection of the cleavage products.

The method may be based on fluorescent chemical cleavage mismatch analysis which is described for example in *PCR Methods and Applications* 3:268–71 (1994) and *Proc. Natl. Acad. Sci.* 85:4397–4401 (1998).

In one embodiment the polynucleotide agent is able to act as a primer for a PCR reaction only if it binds a polynucleotide containing the polymorphism (i.e. a sequence- or allele-specific PCR system). Thus a PCR product will only be produced if the polymorphism is present in the polynucleotide of the individual, and the presence of the polymorphism is determined by the detection of the PCR product. Preferably the region of the primer which is complementary to the polymorphism is at or near the 3' end the primer. In one embodiment of this system the polynucleotide the agent will bind to the wild-type sequence but will not act as a primer for a PCR reaction.

The method may be a Restriction Fragment Length Polymorphism (RFLP) based system. This can be used if the presence of the polymorphism in the polynucleotide creates or destroys a restriction site that is recognized by a restriction enzyme. Thus treatment of a polynucleotide that has such a polymorphism will lead to different products being produced compared to the corresponding wild-type sequence. Thus the detection of the presence of particular restriction digest products can be used to determine the presence of the polymorphism.

The presence of the polymorphism may be determined based on the change that the presence of the polymorphism makes to the mobility of the polynucleotide or protein during gel electrophoresis. In the case of a polynucleotide single-stranded conformation polymorphism (SSCP) analysis may be used. This measures the mobility of the single stranded polynucleotide on a denaturing gel compared to the corresponding wild-type polynucleotide, the detection of a difference in mobility indicating the presence of the polymorphism. Denaturing gradient gel electrophoresis (DGGE) is a similar system where the polynucleotide is electrophoresed through a gel with a denaturing gradient, a difference in mobility compared to the corresponding wild-type polynucleotide indicating the presence of the polymorphism.

The presence of the polymorphism may be determined using a fluorescent dye and quenching agent-based PCR assay such as the TAQMAN™ PCR detection system. In another method of detecting the polymorphism a polynucleotide comprising the polymorphic region is sequenced across the region which contains the polymorphism to determine the presence of the polymorphism.

Various other detection techniques suitable for use in the present methods will be apparent to those conversant with methods of detecting, identifying, and/or distinguishing polymorphisms. Such detection techniques include but are not limited to direct sequencing, use of "molecular beacons" (oligonucleotide probes that fluoresce upon hybridization, useful in real-time fluorescence PCR; see e.g., Marras et al., Genet Anal 14:151 (1999)); electrochemical detection (reduction or oxidation of DNA bases or sugars; see U.S. Pat. No. 5,871,918 to Thorp et al.); rolling circle amplification (see, e.g., Gusev et al., Am J Pathol 159:63 (2001)); Third Wave Technologies (Madison Wis.) INVADER® non-PCR based detection method (see, e.g., Lieder, Advance for Laboratory Managers, 70 (2000))

Accordingly, any suitable detection technique as is known in the art may be utilized in the present methods.

As used herein, "determining" a subject's genotype does not require that a genotyping technique be carried out where a subject has previously been genotyped and the results of the previous genetic test are available; determining a subject's genotype accordingly includes referring to previously completed genetic analyses.

The present invention also provides for a predictive (patient care) test or test kit. Such a test will aid in the therapeutic use of pharmaceutical compounds, including NRTIs, such as abacavir, based on pre-determined associations between genotype and phenotypic response to the therapeutic compound. Such a test may take different formats, including:

(a) a test which analyzes DNA or RNA for the presence of pre-determined alleles and/or polymorphisms. An appropriate test kit may include one or more of the following reagents or instruments: an enzyme able to act on a polynucleotide (typically a polymerase or restriction enzyme), suitable buffers for enzyme reagents, PCR primers which bind to regions flanking the polymorphism, a positive or negative control (or both), and a gel electrophoresis apparatus. The product may utilise one of the chip technologies as described by the state of the art. The test kit would include printed or machine readable instructions setting forth the correlation between the presence of a specific genotype and the likelihood that a subject treated with a specific pharmaceutical compound will experience a hypersensitivity reaction;

(b) a test which analyses materials derived from the subject's body, such as proteins or metabolites, that indicate the presence of a pre-determined polymorphism or allele. An appropriate test kit may comprise a molecule, aptamer, peptide or antibody (including an antibody fragment) that specifically binds to a predetermined polymorphic region (or a specific region flanking the polymorphism). The kit may additionally comprise one or more additional reagents or instruments (as are known in the art). The test kit would also include printed or machine-readable instructions setting forth the correlation between the presence of a specific polymorphism or genotype and the likelihood that a subject treated with a specific synthetic nucleoside analog will experience a hypersensitivity reaction.

Suitable biological specimens for testing are those which comprise cells and DNA and include, but are not limited to blood or blood components, dried blood spots, urine, buccal swabs and saliva. Suitable samples for HLA serologic testing are well known in the art.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

EXAMPLES

Example 1

Study Design

A retrospective, case-control study was conducted with adult (>18 years of age) HIV-infected subjects who participated in a Glaxo Wellcome abacavir clinical development program. Subjects were classified as either "case" or "control" subjects based on the following. Case subjects had experienced an episode of suspected or confirmed hypersensitivity to abacavir; control subjects had received Abacavir for at least six weeks, but had not experienced an episode of confirmed or suspected HSR. The six-week treatment period was chosen based on the knowledge that the majority of HSR events occur within the first six weeks of treatment. Case narratives were collected at or close to the time of the suspected or confirmed hypersensitivity reaction. Control subjects were matched for study (if possible) ethnicity, gender, CD4+ cell count (if available; four CD4+ ranges: <50, 50–200, 201–500, >500 cells/mm3); and age (plus or minus 5 years). Wherever possible, treatment regime was also matched ("näive to treatment" vs. treatment experienced).

Data collection included demography (age, gender, race, CDC classification for HIV infection); history of allergy to medicines and food, drug rashes, asthma, eczema, hay fever, etc.; antiretroviral therapy (ART) and concomitant medications taken at the time of the HSR (or, for controls, during the first six weeks of abacavir treatment).

Case Control Status, Demographics, and Allergy History are provided in Tables 1, 2, and 3.

TABLE 1

Case-Control Status (N = 123)

| Case-Control Status | No. of Pairs | No. of Subjects |
|---|---|---|
| 1 Case-2 Controls | 16 | 48 (39%) |
| 1 Case-1 Control | 14 | 28 (23%) |
| 1 Case-3 Controls | 1 | 4 (3%) |
| 1 Case-0 Control | 14 | 14 (11%) |
| 0 Case-1 Control | 15 | 15 (12%) |
| 0 Case-2 Controls | 7 | 14 (11%) |

TABLE 2

Demographics

| | Cases (N = 45) | Controls (N = 78) |
|---|---|---|
| Age, mean (range) | 42 (29–63) | 40 (30–62) |
| Age (years) | | |
| 18–35 | 15 (34%) | 27 (35%) |
| 35–54 | 25 (57%) | 49 (63%) |
| >54 | 4 (9%) | 2 (3%) |
| Gender | | |
| Male | 40 (89%) | 70 (90%) |
| Female | 5 (11%) | 8 (10%) |

TABLE 3

Allergy History

| | Cases (N = 45) | Controls (N = 78) |
|---|---|---|
| Any Allergy | 33 (73%) | 46 (59%) |
| Allergy to Sulfa Drugs | 14 (31%) | 14 (18%) |
| Any NNRTI* allergy | 9 (20)% | 4 (5%) |
| History of rash to other drugs | 13 (29%) | 14 (18%) |

Polymorphisms in a number of candidate genes were examined. Polymorphisms examined in the TNFα gene included G(-237)A. The presence or absence of the HLA-B57 allele was also examined.

Example 2

Screening TNFα

The presence of the TNFα G(-237A) polymorphism may be determined using a fluorescent dye and quenching agent-based PCR assay, such as the allele discrimination form of the 5' nuclease assay (Lee and Bloch, Nucleic Acids Research 21:3761 (1993)). In brief, this assay uses two allele specific probes labeled differentially with fluorescent "reporter" dyes at the 5' ends and with a common quenching agent at the 3' ends. Normally the fluorescence of each reporter dye is quenched by the quenching agent when present in the same oligonucleotide molecule. The allele specific probes are used in conjunction with two primers, one of which hybridizes to the template 5' of allele specific probes while the other hybridizes to the template 3' of the such probes.

The presence of the TNFα G(-237)A polymorphisms was determined by the method of allelic discrimination using the 5'-nuclease assay. Two allele specific probes labeled with a different fluorescent dye at the 5' ends, but with a common quenching agent at the 3' ends, were used:

```
TNFα G(-237)A-G:
FAM-CCTGCTCCGATTC (MGB)              (SEQ ID NO:9)

TNFα G(-237)A-A:
VIC-CCCTGCTCTGATTC (MGB)             (SEQ ID NO:10)
```

Both probes had a 3' phosphate group so that the thermostable polymerase, AmpliTaq Gold™ polymerase, could not add nucleotides to them. The two allele specific probes were designed using specialized computer software as is known in the art, such that certain properties (melting temperature, GC content, position of the polymorphic base, location within the amplicon) were matched as far as possible, only allowing complete hybridisation to the template DNA when the allele specific polymorphic base was present.

The allele specific probes were used in conjunction with two primers, one of which hybridized to the template 5' of the two allele-specific probes, whilst the other hybridized to the template 3' of the two probes:

```
TNFα G(-237)A forward:
ATCAGTCAGTGGCCCAGAAGAC               (SEQ ID NO:11)

TNFα G(-237)A reverse:
GGGACACACAAGCATCAAGGATA              (SEQ ID NO:12)
```

If the allele corresponding to one of the specific probes was present, the specific probe hybridized perfectly to the target sequence derived from the template. The thermostable polymerase, extending the primer in a 5' to 3' direction toward the allele specific probe, then removed the nucleotides from the specific probe, releasing both the fluorescent dye and the quenching agent. This resulted in an increase in the fluorescence from the reporter dye no longer in close proximity to the quenching agent.

If the allele specific probe hybridized to the other allele the mismatch at the polymorphic site inhibited the 5' to 3' exonuclease activity of the thermostable polymerase and hence prevented release of the fluorescent reporter dye.

At the end of the thermal cycling PCR, the ABI PRISM™7700 sequence detection system was used to measure the increase in the fluorescence from each specific dye directly in PCR reaction vessels. The information from the reactions was then analyzed. If an individual was homozygous for a particular allele, fluorescence corresponding only to the dye from that specific probe was released, but if the individual was heterozygous, then fluorescence from both dyes increased.

Results of screening for the TNFα G(-237)A polymorphism are shown in Table 4.

TABLE 4

| Genotype | Cases (N = 44) | Controls (N = 76) | p-value |
|---|---|---|---|
| 1,1 (G/G) | 22 (50%) | 71 (93%) | <0.0001 |
| 1,2 (G/A) | 20 (45%) | 4 (5%) | <0.0001 |
| 2,2 (A/A) | 2 (5%) | 1 (1%) | 0.1573 |

Distribution of TNFα G(-237)A by various ethnic groups is shown in Table 5 (based on genetic screening of a commercially available genetic population).

TABLE 5

| | G/G (1,1) N | A/G (1,2) N | A/A (2,2) N | Allele Frequency for G | Allele frequency for A |
|---|---|---|---|---|---|
| Caucasian (N = 88) | 83 | 4 | 1 | 96.6% | 3.4% |
| African American (N = 86) | 73 | 13 | 0 | 92.44% | 7.56% |
| Hispanic (N = 50) | 45 | 5 | 0 | 95.0% | 5.0% |

TABLE 5-continued

|  | G/G (1,1) N | A/G (1,2) N | A/A (2,2) N | Allele Frequency for G | Allele frequency for A |
|---|---|---|---|---|---|
| Asian (N = 30) | 28 | 2 | 0 | 96.7% | 3.3% |
| SW Native American (N = 8) | 5 | 3 | 0 | 81.24% | 18.75% |

In the above study, the presence of an "A" allele (A/A or A/G genotype) occurred more often in Cases, compared to that in controls. The G/G genotype occurred less often in Cases, compared to that in controls.

Example 3

Screening HLA-B57

Genotyping of the HLA-B gene was performed in samples from 120 subjects (44 Cases and 76 Controls) in the research laboratories of the Anthony Nolan Bone Marrow Trust (Royal Free Hospital, London, UK). Typing was primarily conducted using Reference Strand-mediated Conformation Analysis (RSCA; see, e.g., Pel-Freez® Clinical Systems, LLC) as is known in the art. Arguello et al., Reviews in Immunogenetics, 1:209 (1999); Arguello et al., Tissue Antigens, 52:57 (1998). DNA sequencing and Sequence Specific Oligonucleotide Probe (SSOP) techniques (see, e.g., Yoshida et al., Hum Immunol 34:257 (1992); Smith et al., Hum Immunol 55:74 (1997)) were used when necessary as backup techniques to determine HLA genotype.

Of the Cases, 25/44 (57%) were found to have the HLA-B57 allele present (i.e., were either heterozygous or homozygous for the HLA-B57 allele), whereas only 3/76 (4%) of the Controls were found to have the HLA-B57 allele present (each was heterozygous for the HLA-B57 allele). Table 6.

TABLE 6

Allele Frequency-HLA-B57

|  | Cases (N = 44) | Controls (N = 76) | p-value |
|---|---|---|---|
| HLA-B57 present | 25 (57%) | 3 (4%) | <0.0001 |

In subjects having at least one HLA-B57 allele (Cases (n=25) and Controls (n=3)), the subtype of HLA-B57 is shown in Table 7. The most common allele was B*5701 (24/25 or 96% of cases carried at least one copy, as did ⅓ or 33.3% of Controls).

In the present study, the HLA-B57 genotype was found more often in Cases than in Controls.

TABLE 7

HLA-B genotype of Cases and Controls who had at least one HLA-B57 allele

| HLA-B Genotype | No. of Subjects | Percent |
|---|---|---|
| CONTROLS N = 3 | | |
| B*0801, B*5701 | 1 | 33.3% |
| B*4501, B*57031 | 1 | 33.3% |
| B*4801, B*57031 | 1 | 33.3% |
| CASES | | |

TABLE 7-continued

HLA-B genotype of Cases and Controls who had at least one HLA-B57 allele

| HLA-B Genotype | No. of Subjects | Percent |
|---|---|---|
| N = 25 | | |
| B*0702, B*5701 | 4 | 16.0% |
| B*07021, B*5701 | 1 | 4.0% |
| B*1402, B*5701 | 1 | 4.0% |
| B*1801, B*5701 | 1 | 4.0% |
| B*35011, B*5701 | 1 | 4.0% |
| B*3503, B*5701 | 1 | 4.0% |
| B*3701, B*5701 | 1 | 4.0% |
| B*3801, B*5701 | 3 | 12.0% |
| B*4001, B*5701 | 1 | 4.0% |
| B*4102, B*5701 | 1 | 4.0% |
| B*4402, B*5701 | 1 | 4.0% |
| B*44021, B*5701 | 1 | 4.0% |
| B*4403, B*5701 | 1 | 4.0% |
| B*44031, B*5701 | 1 | 4.0% |
| B*44031, B*5704 | 1 | 4.0% |
| B*4901, B*5701 | 1 | 4.0% |
| B*5501, B*5701 | 1 | 4.0% |
| B*5701, B*5701 | 2 | 8.0% |
| B*5701, B*57031 | 1 | 4.0% |

Example 4

Data were obtained from subjects in addition to those reported in the above examples. Additional subjects from the retrospective, case-control study described in Example 1 were screened for the presence of TNFα G(-237)A polymorphism and HLA-B57. Cumulative data (combining results provided in the previous Examples and the additional data) are provided in Tables 8 and 9. Total number of subjects was 161; in five subjects no data were available for TNFα G(-237)A status, and no data was available in three subjects for HLA B57 status.

TABLE 8

TNFα G(-237)A

| Genotype | Cases (N = 57) | Controls (N = 99) | p-value |
|---|---|---|---|
| 1,1 (G/G) | 32 (56%) | 92 (93%) | |
| 1,2 (G/A) | 23 (40%) | 6 (6%) | <0.0001* |
| 2,2 (A/A) | 2 (4%) | 1 (1%) | |

*P-value from the Mantel Haenszel chi-square test indicates a statistically significant difference between the rate of the A allele present among the cases vs. the controls.

TABLE 9

Allele Frequency-HLA-B57

|  | Cases (N = 59) | Controls (N = 99) | p-value |
|---|---|---|---|
| HLA-B57 present | 30 (51%) | 3 (3%) | <0.0001* |
| HLA-B5701 present | 28 (47%) | 1 (1%) | <0.0001 |

*P-value derived from the Mantel Haenszel chi-square test indicates a statistically significant difference between the rate of the HLA B57 present among the cases vs. the controls.

Subjects having at least one HLA-B57 allele (cases=30 and controls=3) were tested to determine the occurrence of the HLA B*5701 subtype. In cases, 28/30 (93%) had at least one B*5701 allele; in controls, 1/3 (33%) had at least one B*5701 allele.

In the present study, the HILA-B57 genotype was found more often in Cases than in Controls.

Example 5

Study Design

Additional data from the retrospective, case-control study as described in Example 1 were analyzed, including information from additional subjects and information regarding additional candidate genes. Examples 5 and 6 are cumulative and include the results provided in the prior Examples as well as additional data. The subjects of the prior examples are a part of the larger population reported in Examples 5 and 6.

A multicenter, retrospective, matched case-control research study was conducted to identify variants of candidate genes associated with abacavir hypersensitivity. Subjects were adult ($\geq$18 years of age) HIV-infected individuals who participated in a GlaxoWellcome (now GlaxoSmithKline (GSK)) abacavir clinical development program. Informed consent was obtained. Subjects were classified as either 'case' or 'control'. The following criteria were used to identify cases:

1. Subjects who experienced symptoms consistent with hypersensitivity to abacavir (see #2 below); these symptoms returned within 12 hours of re-challenge with abacavir; abacavir was permanently discontinued.
2. Subjects who experienced two or more of the following symptoms within 2 days of each other: fever, rash, gastrointestinal symptoms (including nausea, vomiting, diarrhea, abdominal pain) and who permanently discontinued abacavir treatment.
3. Subjects who were diagnosed by a non-GSK physician as having developed "HSR", "allergic reaction", or "anaphylaxis" that was attributed to abacavir and who permanently discontinued abacavir treatment.

Prior to selection of a subject as a 'case', the diagnosis of hypersensitivity to abacavir was reviewed by a GSK physician for consistency with the clinical presentation of hypersensitivity.

Matched Controls: Adult HIV infected subjects (18 years of age) who participated in the GSK abacavir clinical development program and who tolerated abacavir for at least 6 weeks without evidence of a hypersensitivity reaction. Control subjects were matched to a particular case subject on five criteria whenever possible: age (within 5 years), gender, ethnicity, CD4+ cell count, and treatment regimen. Whenever possible, two matched controls were recruited for each case enrolled in the study.

Sample Management and Processing

Blood samples were collected into appropriate blood collection tubes. DNA extraction was performed by DNA Sciences (Morrisville, N.C.), and extracted DNA was sent to GSK for genotyping. With the exception of HLA genotyping, genetic assays were conducted by GSK. HLA typing was performed by the Anthony Nolan Bone Marrow Trust, London, UK. The HLA loci (A, B, and DR) were genotyped by the reverse strand conformational analysis (RSCA) method, using DNA sequencing and sequence-specific oligonucleotide (SSO) hybridization as a back-up (see Example 3). Polymorphic markers other than the HLA loci were genotyped using the allelic discrimination form of the 5' nuclease assay (Applied Biosystems, Foster City, Calif.; see Example 2).

Samples were analyzed for the presence or absence of 114 polymorphic alleles.

Study Subjects

A total of 229 total subjects were enrolled and provided informed consent. Twenty-nine subjects were excluded (samples yielded inadequate DNA and/or subject retrospectively failed to meet the inclusion criteria). Two hundred subjects (85 of 100 cases and 115 of 129 controls) had evaluable data from at least one of the 114 genetic markers. A total of 157 subjects' samples were evaluable for TNF$\alpha$-237; a total of 197 subjects' samples were evaluable for HLA-B.

The study population had a median age of 39.8 (24–65) years, and was predominantly male (92%) and Caucasian (74%). Demographic and baseline characteristics were similar among cases and matched controls. Twenty-seven subjects (14%) were Black, and 21 (11%) were Hispanic (Table 10).

TABLE 10

Summary of Demographic and Baseline Characteristics by Case-Control Status

| Characteristic | Cases N = 85 | Controls N = 115 | Total N = 200 |
|---|---|---|---|
| Age[a] (years) | | | |
| N | 85 | 115 | 200 |
| Median (Range) | 40.3 (29–63) | 39.8 (24–65) | 39.8 (24–65) |
| 18–35 years, n (%) | 24 (28) | 32 (28) | 56 (28) |
| 36–54 years, n (%) | 55 (65) | 78 (68) | 133 (67) |
| $\geq$55 years, n (%) | 6 (7) | 5 (4) | 11 (6) |
| Sex | | | |
| N | 85 | 115 | 200 |
| Male, n (%) | 79 (93) | 105 (91) | 184 (92) |
| Female, n (%) | 6 (7) | 10 (9) | 16 (8) |
| Ethnicity | | | |
| N | 85 | 115 | 200 |
| White, n (%) | 66 (78) | 82 (71) | 148 (74) |
| Black, n (%) | 9 (11) | 18 (16) | 27 (14) |
| Asian, n (%) | 0 | 0 | 0 |
| American Hispanic, n (%) | 7 (8) | 14 (12) | 21 (11) |
| Other, n (%) | 3 (4) | 1 (<1) | 4 (2) |
| CDC Class[a] | | | |
| N | 85 | 114 | 199 |
| A, n (%) | 31 (36) | 43 (38) | 74 (37) |
| B, n (%) | 16 (19) | 22 (19) | 38 (19) |
| C, n (%) | 36 (42) | 45 (39) | 81 (41) |
| Other, n (%) | 2 (2) | 4 (4) | 6 (3) |

[a]At time of abacavir initiation

Fifty of 85 cases (59%) were matched to at least one control and 41% of cases had no matching control (Table 11). Reasons why cases lacked controls included: inability to identify a match and missing data. For the 50 cases and their 80 matched controls, 81% of controls were matched to a case by age within 5 years, 99% by gender, 90% by ethnicity, 4% by CD4 cell counts (primarily due to missing data), and 94% by treatment regimen (or participation in the abacavir expanded access program).

TABLE 11

Summary of Case-Control Status

| HSR Case-Control Status | Number of Matched Groups | Number of Subjects N = 200 n (%) |
|---|---|---|
| 1 HSR Case-2 Controls | 28 | 84 (42.0) |
| 1 HSR Case-1 Control | 21 | 42 (21.0) |
| 1 HSR Case-3 Controls | 1 | 4 (2.0) |
| 1 HSR Case-0 Control | 35 | 35 (17.5) |
| 0 HSR Case-1 Control | 17 | 17 (8.5) |
| 0 HSR Case-2 Controls | 9 | 18 (9.0) |

Example 6

Results

Univariate Analysis of Genetic Association with Hypersensitivity

For each polymorphism, the allele frequencies among cases and controls were calculated using univariate analyses. Polymorphisms (other than HLA polymorphisms) with significantly different frequencies between cases and controls (p-value of 0.05 or less) are identified in Table 12 (Fisher's Exact test or conditional logistic regression analysis of the difference between the rates). The TNF G(-237)A polymorphism was present in 25 of 58 cases (43%) compared to 7 of 99 (7%) of controls.

The univariate analysis of the HLA typing showed six loci with significantly different frequencies in cases and controls (p<0.1, Fisher's Exact Test, Table 13). Of these, the difference in frequency of HLA-B57 was the most significant (p<0.0001). HLA-B57 was present in 39 of 84 (46%) cases versus 4 of 113 (4%) controls.

TABLE 13

Summary of HLA Alleles by Case-Control Status for p-values <0.1[a]

| HLA Allele | Cases N (%) | Controls N (%) | p-value |
|---|---|---|---|
| HLA-A31 | 0 | 6 (6%) | 0.0839 |
| HLA-B08 | 4 (5%) | 15 (13%) | 0.0526 |
| HLA-B57 | 39 (46%) | 4 (4%) | <0.0001 |
| HLA-DRB01 | 6 (10%) | 21 (21%) | 0.0826 |
| HLA-DRB03 | 2 (3%) | 18 (18%) | 0.0060 |
| HLA-DRB07 | 23 (38%) | 21 (21%) | 0.0277 |

[a]Fisher's Exact test.

Among non-HLA polymorphisms, the two polymorphisms with the highest statistical significance were TNFα(-237) and MICA (-9263). The HLA-B, MICA and TNFα genes are closely co-located on chromosome 6, and genotyping results were consistent with high allelic association between HLA-B57 and the TNFα G(-237)A allele.

HLA-B57 and TNFα are closely co-located on chromosome 6, and showed high allelic association (Table 14). All but two cases of hypersensitivity reactions with the TNFα-238A allele were also HLA-B57 positive; five cases of hypersensitivity that were HLA-B57 positive lacked the TNFα-238A allele.

TABLE 12

| Gene (SNP position) | Reference (NCBI dbSNP or GenBank) | Variant[b] | Cases | Controls | p-value |
|---|---|---|---|---|---|
| TNFα (-237) | RS361525 | A2 = A | 25 (43%) | 7 (7%) | <0.0001 |
| TNFα (-308) | RS1800629 | A2 = A | 5 (8%) | 28 (28%) | 0.0024 |
| TNFα (-5,100) | | A2 = G | 8 (13%) | 30 (31%) | 0.0127 |
| MICA (-9,263) | RS1052416 | A1 = A | 48 (92%) | 64 (70%) | 0.0015 |
| | | A2 = G | 19 (37%) | 66 (72%) | <0.0001 |
| MICA (exon 2) | RS1063630 | A1 = T | 40 (83%) | 68 (96%) | 0.0391[c] |
| | | A2 = G | 38 (67%) | 47 (48%) | 0.0297 |
| MICA (exon 3) | RS1051792 | A1 = G | 46 (77%) | 88 (90%) | 0.0384 |
| | | A2 = A | 49 (82%) | 57 (58%) | 0.0029 |
| MICB (exon 2) | RS1065075 | A1 = G | 23 (38%) | 56 (57%) | 0.0334 |
| | | A2 = A | 48 (100%) | 67 (92%) | 0.0423[c] |
| MICB (exon 3) | RS1051788 | A1 = A | 23 (38%) | 56 (58%) | 0.0209 |
| | | A2 = G | 48 (100%) | 65 (93%) | 0.0858[c] |
| ATP-dependent RNA helicase p47 | | A2 = T | 27 (45%) | 63 (66%) | 0.0130 |
| ATP-dependent RNA helicase p47 | RS929138 | A1 = C | 39 (68%) | 37 (39%) | 0.0007 |
| | | A2 = T | 46 (81%) | 91 (96%) | 0.0040 |
| Alcohol Dehydrogenase ADH7 (ADH7-C94T) | Nucleotide 403 in GenBank entry M16286 (5'UTR) | A1 = C | 3 (5%) | 16 (17%) | 0.0431 |
| | | A2 = T | 45 (96%) | 59 (84%) | 0.0606[c] |
| UDP-glucuronosyl-transferase (UGT1A6-A551C) | Nucleotide 765 in GenBank M84130 | A1 = A | 46 (77%) | 59 (60%) | 0.0377 |

[a]Unless otherwise noted, the p-value is based on Fisher's exact test.
[b]A1 = allele 1, A2 = allele 2.
[c]p-value based on conditional logistic regression among cases and their matched controls.

TABLE 14

Summary of HLA-B57 and TNFα-237 Association

| HLA-B57 | TNFα-237 | HSR Cases N (%) | Controls N (%) |
|---|---|---|---|
| Subjects without HLA-B57 | | | |
| N | | 30 | 96 |
| | A Allele | 2 (7) | 5 (5) |
| | Without A Allele | 28 (93) | 91 (95) |
| Subjects with HLA-B57 present | | | |
| N | | 28 | 3 |
| | A Allele | 23 (82) | 1 (33) |
| | Without A Allele | 5 (18) | 2 (67) |

Multivariate Analysis of Genetic Association with Hypersensitivity

Exploratory multivariate analyses were conducted to investigate the contributions of different genetic markers. Conditional logistic regression was performed using a subset of cases having at least one matched control (50 cases and 80 controls, see Table 11). A secondary analysis was performed using logistic regression with all 85 cases and 115 controls, irrespective of matching. These analyses indicated HLA-B57 as the most robust marker of the markers studied for hypersensitivity.

Recursive partitioning was used to investigate whether combinations of variables, including marker alleles, might be acting to significantly modify the risk for abacavir hypersensitivity reaction. HLA-B57 was the most significant predictor of whether a subject was a case or a control (Bonferroni-adjusted p-value <0.0001) (Table 15). Of the 159 subjects with sufficient data for inclusion in the recursive partitioning analysis, 33 (21%) had HLA-B57; of these 30 (91%) were cases. Among the 33 HLA-B57 positive subjects, 31 were DRB03 negative; within this group of 31 subjects, 30 (97%) were cases (Bonferroni adjusted p-value=0.001).

TABLE 15

Summary of Recursive Partitioning Data by HLA

| | HSR Cases N = 84 | Controls N = 113 |
|---|---|---|
| Subjects with ≧1 HLA-B57 allele present, N (%) | 39 (46) | 4 (4) |
| Subjects without HLA-B57 allele, N (%) | 45 (54) | 109 (96) |

A statistically significant association between the presence of HLA-B57 and a history of hypersensitivity to abacavir was found. Also found was an association between the presence of TNF-237A polymorphism and hypersensitivity to abacavir, but this association can almost entirely be accounted for by the presence of HLA-B57. A third polymorphism in the same region, MICA-9263G, was also significant by univariate but not by multivariate analysis.

Subgroup Analysis

Descriptive analyses of demographic subgroups are presented in below. The majority of subjects in this study were White males. As shown in Table 16, 53% of White male cases had at least one HLA-B57 allele, compared to 3% of White male controls. Two of nine cases (22%) of hypersensitivity among Black males were HLA-B57 positive compared to 1 of 16 Black male controls (6%). Among Hispanics and other identified ethnic groups, none of 9 cases were HLA-B57 positive, compared to 1 of 13 controls.

TABLE 16

Summary of HLA-B57 Data by Ethnicity: Males

| Males | Ethnicity | | | |
|---|---|---|---|---|
| | White | Black | Other | Total |
| HSR Cases | | | | |
| N | 60 | 9 | 9 | 78 |
| HLA-B57, n (%) | 32 (53) | 2 (22) | 0 | 34 (44) |
| Controls | | | | |
| N | 74 | 16 | 13 | 103 |
| n (%) | 2 (3) | 1 (6) | 1 (8) | 4 (4) |

The majority of study subjects were male. Of the six female cases enrolled, five were white (Table 17). Four of the five White female cases were HLA-B57 positive compared to none of the six controls. While the association was not statistically tested the trend matches that in White males.

TABLE 17

Summary of HLA-B57 Data by Ethnicity: Females

| Female | Ethnicity | | | |
|---|---|---|---|---|
| | White | Black | Other | Total |
| HSR Cases | | | | |
| N | 5 | 0 | 1 | 6 |
| HLA-B57, n (%) | 4 (80) | 0 | 1 (100) | 5 (83) |
| Controls | | | | |
| N | 6 | 2 | 2 | 10 |
| n (%) | 0 | 0 | 0 | 0 |

The invention claimed is:

1. A method of identifying a male Caucasian human subject at increased risk of experiencing a hypersensitivity reaction to a therapeutic regime of abacavir, comprising:
   (a) performing a genotyping technique on a biological sample from said subject to determine whether the subject's HLA-B genotype includes an allele selected from the HLA-B57 allele and the HLA-B*5701 allele;
   (b) detecting an HLA-B57 allele or an HLA-B*5701 allele; and
   (c) correlating the detection of an HLA-B57 or an HLA-B*5701 allele with an increased risk of experiencing a hypersensitivity reaction to a therapeutic regime of abacavir compared to the risk if no HLA-B57 or HLA-B*5701 allele were detected.

2. A method according to claim 1, where said subject has not previously been treated with abacavir.

3. A method according to claim 1, where said subject has previously been treated with abacavir.

4. A method according to claim 1, where one or two copies of the HLA-B57 allele is detected.

5. A method according to claim 1, further comprising determining the presence of a polymorphism in the TNFα gene, where said TNFα polymorphism has been associated with an increased risk of abacavir hypersensitivity reaction.

6. A method according to claim 1 where said HLA genotype is determined by a method that detects the presence of the allelic DNA sequence.

7. A method according to claim 1 where said subject is infected with the Human Immunodeficiency Virus-1 (HIV-1).

8. A method according to claim 1, where an HLA-B*5701 allele is detected.

9. A method of identifying a male Caucasian human subject at increased risk of experiencing a hypersensitivity reaction to a therapeutic regime of abacavir, comprising:
   (a) performing a genotyping technique on a biological sample from said subject to determine whether the subject's HLA-B genotype includes an allele selected from the HLA-B57 allele and the HLA-B*5701 allele;
   (b) detecting an HLA-B57 allele or an HLA-B*5701 allele; and
   (c) identifying said subject as at increased risk of experiencing a hypersensitivity reaction to a therapeutic regime of abacavir compared to the risk if no HLA-B57 or HLA-B*5701 allele were detected.

10. A method according to claim 9, where said subject has not previously been treated with abacavir.

11. A method according to claim 9, where said subject has previously been treated with abacavir.

12. A method according to claim 9, where one or two copies of the HLA-B57 allele is detected.

13. A method according to claim 9, further comprising determining the presence of a polymorphism in the TNFα gene, where said TNFα polymorphism has been associated with an increased risk of abacavir hypersensitivity reaction.

14. A method according to claim 9 where said HLA genotype is determined by a method that detects the presence of the allelic DNA sequence.

15. A method according to claim 9 where said subject is infected with the Human Immunodeficiency Virus-1 (HIV-1).

16. A method according to claim 1, where an HLA-B*5701 allele is detected.

17. A method according to claim 1, wherein said biological sample is selected from the group consisting of cells, blood, blood components, urine and saliva.

18. A method according to claim 9, wherein said biological sample is selected from the group consisting of cells, blood, blood components, urine and saliva.

* * * * *